(12) United States Patent
Nygren, Jr.

(10) Patent No.: US 7,464,716 B1
(45) Date of Patent: Dec. 16, 2008

(54) TWO HANDED POWER DRIVEN FLOSSING APPARATUS WITH REMOVABLE HEAD FOR ATTACHMENT TO POWER DRIVEN TOOTHBRUSH

(76) Inventor: William D. Nygren, Jr., 641 S. Downing St., Denver, CO (US) 80209

( * ) Notice: Subject to any disclaimer, the term of this patent is extended or adjusted under 35 U.S.C. 154(b) by 335 days.

(21) Appl. No.: 11/136,351

(22) Filed: May 24, 2005

Related U.S. Application Data

(60) Provisional application No. 60/582,773, filed on Jun. 25, 2004.

(51) Int. Cl.
*A61C 15/00* (2006.01)
(52) U.S. Cl. ..................... 132/322
(58) Field of Classification Search .......... 132/321–329
See application file for complete search history.

(56) References Cited

U.S. PATENT DOCUMENTS

| | | | | |
|---|---|---|---|---|
| 1,559,320 | A | 10/1925 | Hirsh | |
| 3,759,274 | A | 9/1973 | Warner | 132/92 R |
| 3,799,177 | A * | 3/1974 | Bragg | 132/326 |
| 4,162,687 | A | 7/1979 | Lorch | 132/91 |
| 4,265,257 | A | 5/1981 | Salyer | 132/92 R |
| 4,655,233 | A * | 4/1987 | Laughlin | 132/323 |
| 4,807,651 | A | 2/1989 | Naydich | 132/323 |
| 4,920,993 | A * | 5/1990 | Mackie | 132/324 |
| 5,184,632 | A * | 2/1993 | Gross et al. | 132/326 |
| 5,199,452 | A * | 4/1993 | Cheng | 132/325 |
| 5,267,579 | A | 12/1993 | Bushberger | 132/322 |
| 5,279,314 | A | 1/1994 | Poulos et al. | 132/322 |
| 5,305,768 | A | 4/1994 | Gross et al. | 132/321 |
| 5,564,446 | A * | 10/1996 | Wiltshire | 132/323 |
| 5,692,532 | A * | 12/1997 | Gabrovsek | 132/325 |
| 5,896,867 | A | 4/1999 | McGaha et al. | 132/321 |
| 6,019,109 | A | 2/2000 | Moore | 132/323 |
| 6,047,711 | A | 4/2000 | Wagner | 132/322 |
| 6,112,753 | A | 9/2000 | Arsenault | 132/323 |
| 6,526,994 | B1 | 3/2003 | Santoro | 132/322 |
| 6,874,509 | B2 | 4/2005 | Bergman | 132/325 |
| 2002/0178519 | A1 * | 12/2002 | Zarlengo | 15/22.2 |
| 2004/0134511 | A1 | 7/2004 | Bergman | 132/322 |
| 2004/0244814 | A1 | 12/2004 | Prineppi | 132/322 |

* cited by examiner

*Primary Examiner*—Robyn Doan
*Assistant Examiner*—Rachel A Running
(74) *Attorney, Agent, or Firm*—Marsh Fischmann & Breyfogle LLP

(57) ABSTRACT

An electric flossing apparatus comprising a flossing head which is detachably connected to a handle containing a reciprocating drive unit, a non-powered second handle to allow for the increased controllability of two-handed powered flossing and a disposable floss assembly that can be easily be attached to or released from the flossing head and handle. The floss is releasably attached to the flossing head in a manner that allows reciprocating motion to be imparted along the length of the floss no matter which direction that the floss exits the end of the flossing head or the shape of the path it takes. By using both hands for flossing the floss may be pulled straight and tensioned to facilitate insertion between tightly spaced teeth and then wrapped around a tooth to facilitate cleaning of the front, sides, and back of each tooth above, near, or just below the gum line. The reciprocating motion is imparted to the floss whenever the floss is tensioned. The intensity of the motion is then controlled by the amount of tension and the "rigidity" of the users grip on the two handles. The drive unit handle assembly may be from an inexpensive commercially available electric toothbrush such as a Crest Spinbrush™.

20 Claims, 15 Drawing Sheets

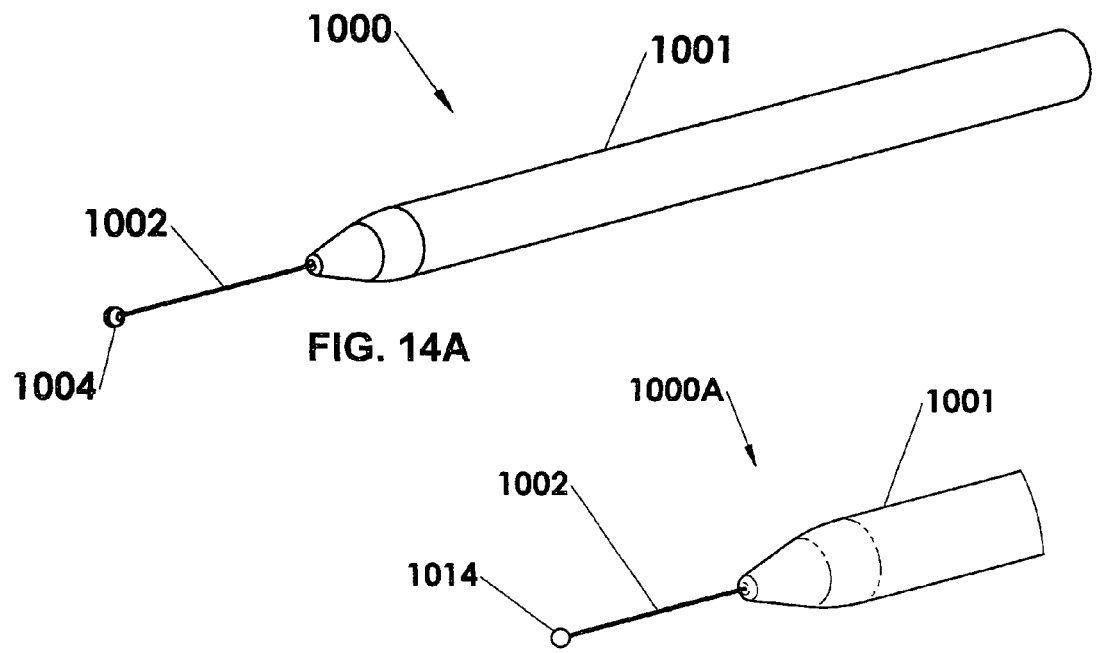
FIG. 14A
FIG. 14B
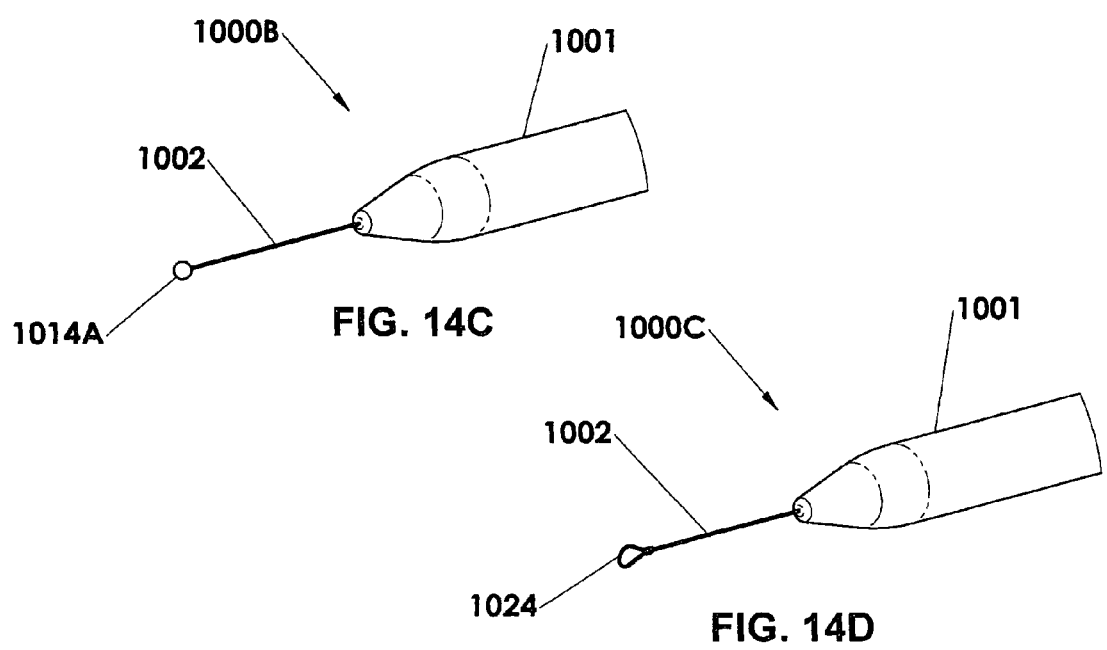
FIG. 14C
FIG. 14D

TWO HANDED POWER DRIVEN FLOSSING APPARATUS WITH REMOVABLE HEAD FOR ATTACHMENT TO POWER DRIVEN TOOTHBRUSH

CROSS-REFERENCE TO RELATED APPLICATIONS

This patent application claims priority under 35 U.S.C. §119 to U.S. Provisional Patent Application Ser. No. 60/582,773, that is entitled "FLOSSING APPARATUS", that was filed on Jun. 25, 2004, and the entire disclosure of which is being incorporated by reference herein.

FIELD OF THE INVENTION

The present invention relates generally to electric tooth flossing devices. More particularly, it relates to an improved two-handed powered flossing device which detachably connects to a drive unit which can also be used to power an electric toothbrush.

BACKGROUND OF THE INVENTION

The dental profession has long recommended cleaning one's teeth with dental floss as a necessary part of daily dental hygiene. It is widely recognized that the proper use of dental floss is an effective means for preventing the buildup of plaque, gum disease and tooth decay.

Dental hygienists typically recommend wrapping a short length dental floss around the forefinger of each hand and holding this in place with the thumbs. The floss is then pulled tight and inserted into the gaps between each pair of teeth and moved up and down while wrapping the floss around the sides of the teeth as much as possible. The purpose of this wrapping action is to disturb the plaque and clean at the gum line not only between the teeth, but also around the corners and along the sides of the teeth.

This flossing operation, while necessary for dental health, is often neglected in practice because of the difficulty of holding onto the wet saliva-coated floss, the difficulty and clumsiness of inserting a major portion of both hands into the back of the mouth and finally, the difficulty of pulling the floss between tightly spaced teeth.

Both non-powered and powered flossing devices have attempted to alleviate these problems. Generally, there are one-handed units which incorporate a "V" shaped floss holder designed to eliminate the difficulty of holding the floss by the finger and thumb method. Although these one-handed devices appear to be a simple solution, they, in fact, greatly restrict the ability to wrap the floss around and clean the sides of the teeth. Many of these one-handed devices also incorporate rather complicated methods for attaching, replacing or advancing used floss across the "V" of the flossing device. At least some powered units generally incorporate the "V" shaped floss holder with all of its drawbacks, while adding vibratory motion to aid in plaque disruption and cleaning. The difficulty with this motion is that if the floss is loose enough to wrap around the teeth for proper cleaning, then the vibratory motion of the yoke may not be oriented such that it is able to induce to desired reciprocating motion of the floss along its length.

The prior art contains many patents similar to U.S. Pat. Nos. 5,279,414 and 5,267,579 which have these "V" shaped yokes for tightly holding a short length of floss and imparting a vibratory or oscillating motion to it. The floss is either tied onto the yoke as in the case of U.S. Pat. No. 5,267,579, or the yoke with a short length of floss is made to be detachable and disposable. The problem with flossers of this type is that the floss must be installed tightly across the open end of the "V" shaped yoke and so the floss cannot be wrapped around the tooth for proper cleaning. If the floss is installed loosely across the "V" shaped yoke, then, during floss insertion, the yoke will contact the teeth before the floss becomes tight. This contact between the yoke and teeth will make it difficult if not impossible to insert the floss between the teeth and no useful motion will be imparted to the floss.

U.S. Pat. No. 6,019,109 presents a non-powered, two handed flosser with floss wrapped around the ends of the two flossing handles. During flossing, the floss is unwrapped from one handle and wrapped onto the other. The problem with this device is that it is very difficult to insert the floss between teeth and to thoroughly clean them without the assistance of rapid powered floss motion. Also, since the floss is just wrapped around the ends of the handles, any attempt to pull the floss tight while wrapping the floss in a "U" shape around a tooth is likely to pull the floss off of the end of the coil of floss.

U.S. Pat. No. 4,265,257 is a powered flosser with a removable arm or handle that can be used for two handed flossing. This device has at least three problems. First, the floss is not easily replaceable. Second, the floss is in a V-shape between the powered and non-powered handles, making it awkward if not impossible to wrap the floss around the teeth. Third, the powered handle imparts a lateral vibratory motion to the floss "arm," so that even if the floss could be wrapped in a "U" shape around a tooth, it would be essentially parallel to the flosser "arm" at its attachment point, and so almost no reciprocating motion could be imparted to the floss when it is most needed.

U.S. Pat. No. 6,047,711 presents a device used to convert an electric toothbrush into a power-driven flossing device. This flossing device also uses a "V" shaped yoke to hold the floss, and in addition, the yoke has conical apertures at the tip of each leg of the "V" that accept and hold a length of floss with a bead at each end. The floss is attached by pressing the legs of the "V" shaped yoke towards each other enough to allow insertion of a bead into each aperture. When the yoke is released the legs of the "V" pull the floss tight across the yoke. Here again, the floss must remain tight across the yoke in order to remain attached to the flossing device.

Accordingly it has been considered desirable to develop a new and improved electric flossing device which would overcome the foregoing difficulties and others while providing better and more advantageous overall results.

SUMMARY OF THE INVENTION

A general object of the present invention is to provide an electric dental flosser that is easy to use, safe, and overcomes the limitations and drawbacks of the prior art.

A specific object of the present invention is to provide an electric dental flosser with inexpensive disposable floss assemblies for sanitation purposes and ease of attachment and replacement.

Another specific object of the present invention is to provide a simple dental flossing head that is easily attached to the power unit of an inexpensive electric toothbrush.

Yet another specific object of the present invention is to provide a two-handed electric dental flossing apparatus that allows the floss to not only be easily inserted between the teeth when pulled taught, but also to be easily wrapped around the corners and sides of the teeth and tensioned.

Still another specific object of the present invention is to provide a two-handed electric dental flossing apparatus that generates reciprocating motion of the floss regardless of the orientation or angle that the floss exits the tip of the flossing head or the shape of the path that the floss takes along its length.

Yet one more specific object of the present invention is to provide a two-handed electric dental flossing apparatus that allows the strength of the reciprocating motion of the floss to be easily controlled by the tension applied to the floss and the rigidity of the grip on the flossing handles.

Yet another specific object of the present invention is to provide a two-handed electric dental flossing apparatus that allows the floss to not only be easily inserted between the teeth when pulled taught, but also to be easily wrapped around the corners and sides of the teeth while maintaining the reciprocating motion along the length of the floss.

In accordance with the present invention, an electric dental flosser is powered by a drive unit which includes an electric motor energized by a replaceable or rechargeable battery power source. A conventional spur gear reduction gearbox coupled to a scotch yoke mechanism reduces the speed of the motor and produces the desired reciprocating motion required to drive the flossing head. The motor is connected to the battery through a waterproof switch.

Removable flossing head units attach to the drive unit, which also serves as a handle for the assembled flosser. The flossing head attaches to the drive unit by the use of protrusions which fit into L-shaped slots in the drive unit. The reciprocating output shaft of the drive unit simultaneously attaches to the flossing head drive shaft in a similar fashion.

The flossing head has an inner stationary portion which attaches to the drive unit housing and an inner moving portion which attaches to the drive unit output shaft. The flossing head also has an outer moving portion which facilitates attachment of the disposable floss. The inner moving portion links the reciprocating motion of the drive unit's output shaft to the floss connection fitting.

The floss connection fitting is exposed by retracting the external moving portion of the flossing head axially towards the drive unit against the force of a spring. The spring normally holds the external portion of the flossing head away from the drive unit against a stop. With the flossing head retracted, the floss connection fitting is exposed so that the floss assembly can be attached.

The floss assembly consists of a short length of floss with small end fittings tied or otherwise attached to each end of the floss.

After the floss assembly end fitting is engaged with the floss connection fitting, the internal spring is again allowed to push the outer moving portion of the flossing head away form the drive unit, and in so doing trap the floss end fitting inside the tip of the flossing head. Release of the floss assembly is simply the reverse of the attachment process.

The non-powered handle which completes the flossing apparatus can be either reusable of disposable. In the case of the reusable non-powered handle, the internal mechanism may be identical to that of the flossing head, except that the drive shaft is identical to that of the powered flossing head. In the case of the disposable non-powered handle, the floss assembly is permanently attached to the disposable handle, thus eliminating the internal linkage and attachment fitting.

When operating the dental flosser, the user moves the power switch to the "on" position and inserts the floss assembly between two teeth using both the powered flossing head and the non-powered handle similar to the manual method, but without having to insert the hands into the mouth. By pulling the floss tight between the tips of the two units and adjusting the tension applied, the desired magnitude of floss reciprocation can be controlled. This reciprocation greatly reduces the force required to insert the floss between tightly spaced teeth and so reduces the chance that the floss will "snap" down between the teeth and damage the gums.

Once the floss is inserted between the teeth, it can be moved up and down to clean between the teeth and disturb any plaque which is trying to attach to the teeth surfaces.

Next, due to the added flexibility and controllability of a two handed flossing device, the floss may be wrapped around the corners and sides of the teeth as well as moved up and down. With the floss pulled tight while wrapped around the tooth, the user can again control the vigor of the reciprocating motion of the floss, which greatly adds to the cleaning action of the up and down motion of the floss applied manually.

A number of additional aspects of the invention will now be described. Each of these aspects is believed to be a new and non-obvious combination of features in the flossing art. Although each of these aspects is described with the dental floss as being part thereof, it should be appreciated that each of these aspects may be presented without positively requiring the dental floss, and instead merely using the dental floss to describe the various features of a flosser.

A first aspect of the present invention is generally directed to a flossing device. This flossing device includes dental floss, as well as first and second handles that are independently maneuverable by a user when flossing. The first handle is "powered" in that it includes a drive and a drive shaft. The drive shaft is interconnected with the drive such that it axially reciprocates during operation of the drive. The dental floss is appropriately interconnected with the second handle, and is also appropriately interconnected with the drive shaft of the first handle. A portion of the dental floss extends between the first and second handles and may be disposed between a pair of adjacent teeth when the user is flossing.

Various refinements exist of the features noted in relation to the first aspect of the present invention. Further features may also be incorporated in the first aspect of the present invention as well. These refinements and additional features may exist individually or in any combination. The first and second handles each may be of any appropriate configuration. However, it may be desirable for each handle to have a tip that is angled relative to its main body section in a single dimension or reference plane. In one embodiment, the first handle is in the form of a power unit having a drive of any appropriate size/shape/configuration, as well as a flossing head that is detachably interconnected with the power unit. This "power unit" may be from a commercially available powered toothbrush, where the flossing head attachment associated with the first aspect would simply replace the toothbrush attachment of this powered toothbrush. Although the second handle could be of the same configuration as the first handle, such need not be the case. For instance, the second handle may be non-powered.

The first handle may include a first aperture that has a closed perimeter (e.g., in the form of an eyelet). The dental floss may extend through this first aperture in order to interconnect with the drive shaft. Generally, this allows the first handle to be disposed in virtually any position and yet still have the dental floss be moved in a desired manner by the axially reciprocating drive shaft. The second handle similarly may include a second aperture that has a closed perimeter, and the dental floss may extend through this second aperture in order to interconnect with the second handle. In one embodiment, the noted apertures are included on the distal ends of the first and second handles, and are defined by a bore that extends within the respective handle (i.e., the "closed perimeter" would coincide with the bore sidewall).

A number of characterizations may be made in relation to the interconnection of the dental floss with the first and second handles. One is that the dental floss may be detachably coupled with both the second handle and the drive shaft of the first handle. Another is that the "point of interconnection" of the dental floss with each of the first and second handles may remain within the interior of the first and second handles during operation of the flossing device (e.g., recessed within the handles). In one embodiment, the dental floss includes a pair of fittings, and each of the first and second handles includes a fitting. The fitting of the first handle is interconnected with its drive shaft and is detachably coupled with one of the dental floss fittings, while the fitting of the second handle is detachably coupled with the other dental floss fitting. The axial reciprocation of the drive shaft may move the dental floss fitting (e.g., axially) that is detachably coupled with the fitting of the first handle to move the dental floss in a desired manner for flossing operations. In another embodiment, the dental floss includes a fitting for detachably coupling with the first handle, but is fixed to the second handle (e.g., where the second handle and the fixed dental floss are a disposable unit).

In accordance with the foregoing, any pair of the above-noted detachably coupled fittings may remain recessed within the interior of their respective handle during operation of the flossing device. The first and second handles may be configured such that their fittings can also be exposed to allow for a dental floss fitting to be coupled or decoupled from this handle fitting. In one embodiment, each of the first and second handles includes a pair of sections that are movably interconnected in any appropriate manner. The handle fitting may remain in a fixed position relative to one of these sections of a given handle at least when coupling or decoupling the dental floss from this handle. Providing relative movement between these two sections of a given handle will then expose the corresponding handle fitting. A subsequent relative movement between these same two sections in the opposite direction could then be used to retract the handle fitting, along with any coupled dental floss fitting, back within the handle. It should be appreciated that the first handle may include a pair of the noted movable sections, regardless of the configuration of the second handle (e.g., the first handle may be of the noted configuration, with the dental floss and the second handle being a disposable unit).

A second aspect of the present invention is generally directed to a flossing device. This flossing device includes dental floss, as well as first and second handles that are independently maneuverable by a user when flossing. The dental floss is appropriately interconnected with the first and second handles such that a portion of the dental floss extends between the first and second handles for disposition between a pair of adjacent teeth when the user is flossing. The dental floss includes at least one fitting, and at least the first handle includes a fitting. The fitting of the first handle is disposable in each of a coupling/decoupling position where the fitting is exposed for coupling or decoupling with a dental floss fitting, as well as in an operating position where a coupled handle fitting and dental floss fitting remain recessed within the respective handle during flossing operations.

Various refinements exist of the features noted in relation to the second aspect of the present invention. Further features may also be incorporated in the second aspect of the present invention as well. These refinements and additional features may exist individually or in any combination. The first and second handles each may be of any appropriate configuration. However, it may be desirable for each handle to have a tip that is angled relative to its main body section in a single dimension or reference plane. Although the second handle could be of the same configuration as the first handle, such need not be the case. For instance, the first handle may be powered, while the second handle may be non-powered. In one embodiment, the dental floss includes another fitting for detachably coupling with a fitting of the second handle in the same manner as the first handle. In another embodiment, the dental floss is fixed to the second handle (e.g., where the second handle and the fixed dental floss are a disposable unit).

The first handle may be "powered" in that it may include a drive and a drive shaft. The drive shaft may be interconnected with the drive such that it axially reciprocates during operation of the drive. The fitting of the first handle that detachably couples with a dental floss fitting may be interconnected with this drive shaft such that this fitting moves (e.g., axially) along with the drive shaft to impart a desired motion to the dental floss. More generally, the fitting of the first handle may be interconnected with a drive that moves this fitting relative to an end of the first handle that is disposed within the user's mouth when flossing, to in turn move the dental floss. In one embodiment, the first handle is in the form of a power unit having a drive of any appropriate size/shape/configuration, as well as a flossing head that is detachably interconnected with the power unit. This "power unit" may be from a commercially available powered toothbrush, where the flossing head attachment associated with the second aspect would simply replace the toothbrush attachment of this powered toothbrush.

The first handle may include a first aperture that has a closed perimeter (e.g., in the form of an eyelet). The dental floss may extend through this first aperture such that one of its fittings is detachably coupled with the fitting of the first handle at an interior location. When the first handle is powered, this allows the first handle to be disposed in virtually any position and yet still have the dental floss be moved in a desired manner. The second handle similarly may include a second aperture that has a closed perimeter, and the dental floss may extend through this second aperture for interconnection with the second handle at an interior location. In one embodiment, the noted apertures are included on the distal ends of the first and second handles, and are defined by a bore that extends within the respective handle (i.e., the "closed perimeter" would coincide with the bore sidewall).

A number of characterizations may be made in relation to the interconnection of the dental floss with the first and second handles. One is that the dental floss may be detachably coupled with each of the first and second handles. Another is that the "point of interconnection" of the dental floss with each of the first and second handles may remain within the interior of the first and second handles during operation of the flossing device (e.g., recessed within the handles). In accordance with the foregoing, any pair of the above-noted detachably coupled fittings may remain recessed within the interior of their respective handle during operation of the flossing device. The first and second handles may be configured with fittings that can also be exposed to allow for a dental floss fitting to be coupled or decoupled from this handle fitting. In one embodiment, each of the first and second handles includes a pair of sections that are movably interconnected in any appropriate manner. The handle fitting may remain in a fixed position relative to one of these sections of a given handle at least when coupling or decoupling the dental floss from this handle. Providing relative movement between these two sections of a given handle will then expose the corresponding handle fitting. It should be appreciated that the first handle may include a pair of the noted movable sections, regardless of the configuration of the second handle (e.g., the first handle may be of the noted configuration, with the dental floss and the second handle being a disposable unit).

A third aspect of the present invention is generally directed to a flossing device. This flossing device includes dental floss, as well as first and second handles that are independently maneuverable by a user when flossing. The dental floss is appropriately interconnected with the first and second handles such that a portion of the dental floss extends between the first and second handles for disposition between a pair of adjacent teeth when the user is flossing. In this regard, the dental floss includes a pair of fittings, and each of the first and second handles includes a fitting.

The first handle of the third aspect further includes a drive, as well as a first aperture having a closed perimeter. The fitting of the first handle is extendable through this first aperture to allow it to be coupled or decoupled with one of the dental floss fittings. This first pair of coupled fittings may be directed back through the first aperture and into the interior of the first handle, where this first pair will remain during flossing operations. Similarly, the second handle of the third aspect also may include a second aperture having a closed perimeter. The fitting of the second handle is extendable through this second aperture to allow it to be coupled or decoupled with the other of the dental floss fittings. This second pair of coupled fittings may be directed back through the second aperture and into the interior of the second handle, where this second pair will remain during flossing operations.

Various refinements exist of the features noted in relation to the third aspect of the present invention. Further features may also be incorporated in the third aspect of the present invention as well. These refinements and additional features may exist individually or in any combination. The first and second handles each may be of any appropriate configuration. However, it may be desirable for each handle to have a tip that is angled relative to its main body section in a single dimension or reference plane. Although the second handle could be of the same configuration as the first handle, such need not be the case. For instance, the second handle may be powered or non-powered.

The first handle is "powered" and may include a drive shaft. The drive shaft may be interconnected with the drive such that it axially reciprocates during operation of the drive. The fitting of the first handle that detachably couples with a dental floss fitting may be interconnected with this drive shaft such that it moves (e.g., axially) along with the drive shaft to impart a desired motion to the dental floss. More generally, the fitting of the first handle may be interconnected with a drive that moves this fitting relative to an end of the first handle that is disposed within the user's mouth when flossing, to in turn move the dental floss. In one embodiment, the first handle is in the form of a power unit having a drive of any appropriate size/shape/configuration, as well as a flossing head that is detachably interconnected with the power unit. This "power unit" may be from a commercially available powered toothbrush, where the flossing head attachment associated with the third aspect would simply replace the toothbrush attachment of this powered toothbrush.

With the first handle being powered and with the dental floss passing through the first aperture of the first handle having the closed perimeter for interconnection with the drive, the first handle may be disposed in virtually any position and yet still have the dental floss be moved in a desired manner. In one embodiment, the noted apertures are included on the distal ends of the first and second handles, and are defined by a bore that extends within the respective handle (i.e., the "closed perimeter" would coincide with the bore sidewall).

A number of characterizations may be made in relation to the interconnection of the dental floss with the first and second handles. One is that the dental floss may be detachably coupled with each of the first and second handles. Another is that the "point of interconnection" of the dental floss with each of the first and second handles may remain within the interior of the first and second handles during operation of the flossing device (e.g., recessed within the handles). In accordance with the foregoing, each pair of the above-noted detachably coupled fittings may remain recessed within the interior of their respective handle during operation of the flossing device. The first and second handles may be configured such that their fittings can also be exposed to allow for a dental floss fitting to be coupled or decoupled from this handle fitting. In one embodiment, each of the first and second handles includes a pair of sections that are movably interconnected in any appropriate manner. The handle fitting may remain in a fixed position relative to one of these sections of a given handle at least when coupling or decoupling the dental floss from this handle. Providing relative movement between these two sections of a given handle will then expose the corresponding handle fitting. A subsequent relative movement between these same two sections in the opposite direction could then be used to retract the handle fitting, along with any coupled dental floss fitting, back within the handle.

A fourth aspect of the present invention is generally directed to a flossing device. This flossing device includes dental floss, as well as first and second handles that are independently maneuverable by a user when flossing. The dental floss is appropriately interconnected with the first and second handles such that a portion of the dental floss extends between the first and second handles for disposition between a pair of adjacent teeth when the user is flossing. In this regard, the dental floss includes at least one fitting, and at least the first handle includes a fitting. At least the first handle includes a pair of sections that are movably interconnected in any appropriate manner. The fitting of the first handle may remain in a fixed position relative to one of these sections at least when coupling or decoupling the dental floss from this fitting. Providing relative movement between these two sections of the first handle will then expose the corresponding handle fitting. At this time, a dental floss fitting may be coupled with or decoupled from the fitting of the first handle. A subsequent relative movement between these same two sections in the opposite direction could then be used to retract the fitting of the first handle, along with any coupled dental floss fitting, back within the first handle.

Various refinements exist of the features noted in relation to the fourth aspect of the present invention. Further features may also be incorporated in the fourth aspect of the present invention as well. These refinements and additional features may exist individually or in any combination. The first and second handles each may be of any appropriate configuration. However, it may be desirable for each handle to have a tip that is angled relative to its main body section in a single dimension or reference plane. Although the second handle could be of the same configuration as the first handle, such need not be the case. For instance, the second handle may be powered or non-powered. In one embodiment, the dental floss includes another fitting for detachably coupling with a fitting of the second handle in the same manner as the first handle. In another embodiment, the dental floss is fixed to the second handle (e.g., where the second handle and the fixed dental floss are a disposable unit).

The first handle may be "powered" in that it may include a drive and a drive shaft. The drive shaft may be interconnected with the drive such that it axially reciprocates during operation of the drive. The fitting of the first handle that detachably couples with a dental floss fitting may be interconnected with this drive shaft such that it moves (e.g., axially) along with the drive shaft to impart a desired motion to the dental floss. More generally, the fitting of the first handle may be interconnected with a drive that moves the fitting relative to an end of the first handle that is disposed within the user's mouth when flossing, to in turn move the dental floss. In one embodiment, the first handle is in the form of a power unit having a drive of any appropriate size/shape/configuration, as well as a flossing head that is detachably coupled with the power unit. This "power unit" may be from a commercially available powered toothbrush, where the flossing head attachment associated with the fourth aspect would simply replace the toothbrush attachment of this powered toothbrush.

The first handle may include a first aperture that has a closed perimeter (e.g., in the form of an eyelet). The dental floss may extend through this first aperture such that one of its fittings is detachably coupled with the fitting of the first handle at an interior location. When the first handle is powered, this allows the first handle to be disposed in virtually any position and yet still have the dental floss be moved in a desired manner. The second handle similarly may include a second aperture that has a closed perimeter, and the dental floss may extend through this second aperture for interconnection with the second handle at an interior location. In one embodiment, the noted apertures are included on the distal ends of the first and second handles, and are defined by a bore that extends within the respective handle (i.e., the "closed perimeter" would coincide with the bore sidewall).

A number of characterizations may be made in relation to the interconnection of the dental floss with the first and second handles. One is that the dental floss may be detachably coupled with each of the first and second handles. Another is that the "point of interconnection" of the dental floss with each of the first and second handles may remain within the interior of the first and second handles during operation of the flossing device (e.g., recessed within the handles). In accordance with the foregoing, any pair of the above-noted detachably coupled fittings may remain recessed within the interior of their respective handle during operation of the flossing device.

A fifth aspect of the present invention is generally directed to a flossing device. This flossing device includes dental floss, as well as first and second handles that are independently maneuverable by a user when flossing. The dental floss is appropriately interconnected with the first and second handles such that a portion of the dental floss extends between the first and second handles for disposition between a pair of adjacent teeth when the user is flossing. In this regard, the dental floss includes at least one fitting, and at least the first handle includes a fitting. The first handle includes a drive, and its fitting is interconnected with and movable by this drive. Coupling one of the dental floss fittings with the fitting of the first handle will thereby move the dental floss.

Various refinements exist of the features noted in relation to the fifth aspect of the present invention. Further features may also be incorporated in the fifth aspect of the present invention as well. These refinements and additional features may exist individually or in any combination. The first and second handles each may be of any appropriate configuration. However, it may be desirable for each handle to have a tip that is angled relative to its main body section in a single dimension or reference plane. Although the second handle could be of the same configuration as the first handle, such need not be the case. For instance, the second handle may be powered or non-powered. In one embodiment, the dental floss includes another fitting for detachably coupling with a fitting of the second handle in the same manner as the first handle. In another embodiment, the dental floss is fixed to the second handle (e.g., where the second handle and the fixed dental floss are a disposable unit).

The first handle is "powered" and may include a drive shaft. The drive shaft may be interconnected with the drive such that it axially reciprocates during operation of the drive. The fitting of the first handle that detachably couples with a dental floss fitting may be interconnected with this drive shaft such that it moves (e.g., axially) along with the drive shaft to impart a desired motion to the dental floss. More generally, the fitting of the first handle may be interconnected with a drive that moves this fitting relative to an end of the first handle that is disposed within the user's mouth when flossing, to in turn move the dental floss. In one embodiment, the first handle is in the form of a power unit having a drive of any appropriate size/shape/configuration, as well as a flossing head that is detachably interconnected with the power unit. This "power unit" may be from a commercially available powered toothbrush, where the flossing head attachment associated with the fifth aspect would simply replace the toothbrush attachment of this powered toothbrush.

The first handle may include a first aperture that has a closed perimeter (e.g., in the form of an eyelet). The dental floss may extend through this first aperture in order to interconnect with the drive. Generally, this allows the first handle to be disposed in virtually any position and yet still have the dental floss be moved in a desired manner by the drive. The second handle similarly may include a second aperture that has a closed perimeter, and the dental floss may extend through this second aperture in order to interconnect with the second handle. In one embodiment, the noted apertures are included on the distal ends of the first and second handles, and are defined by a bore that extends within the respective handle (i.e., the "closed perimeter" would coincide with the bore sidewall).

A number of characterizations may be made in relation to the interconnection of the dental floss with the first and second handles. One is that the dental floss may be detachably coupled with both the second handle and the drive of the first handle. Another is that the "point of interconnection" of the dental floss with each of the first and second handles may remain within the interior of the first and second handles during operation of the flossing device (e.g., recessed within the handles). In accordance with the foregoing, any pair of the above-noted detachably coupled fittings may remain recessed within the interior of their respective handle during operation of the flossing device. The first and second handles may be configured with fittings that can also be exposed to allow for a dental floss fitting to be coupled or de-coupled from this handle fitting. In one embodiment, each of the first and second handles includes a pair of sections that are movably interconnected in any appropriate manner. The handle fitting may remain in a fixed position relative to one of these sections of a given handle at least when coupling or decoupling the dental floss from this fitting. Providing relative movement between these two sections of a given handle will then expose the corresponding handle fitting. A subsequent relative movement between these same two sections in the opposite direction could then be used to retract the handle fitting, along with any coupled dental floss fitting, back within the handle. It should be appreciated that the first handle may include a pair of the noted movable sections, regardless of the configuration of the second handle (e.g., the first handle may be of the noted configuration, with the dental floss and second handle being a disposable unit).

These and other objects, aspects, advantages and features of the present invention will be more fully understood and appreciated upon consideration of the following detailed description of preferred embodiments, presented in conjunction with the accompanying drawings.

BRIEF DESCRIPTION OF THE DRAWINGS

FIG. 14A is a perspective of a first embodiment of a disposable straight non-powered floss handle.

FIG. 14B is a fragmentary perspective of a second embodiment of a disposable straight non-powered floss handle.

FIG. 14C is a fragmentary perspective of a third embodiment of a disposable straight non-powered floss handle.

FIG. 14D is a fragmentary perspective of a fourth embodiment of a disposable straight non-powered floss handle.

DETAILED DESCRIPTION

Reference will now be made to the drawings, wherein the drawings are for the purposes of illustrating various embodiments of the invention only and not for purposes of limiting the same.

Figure 1A:
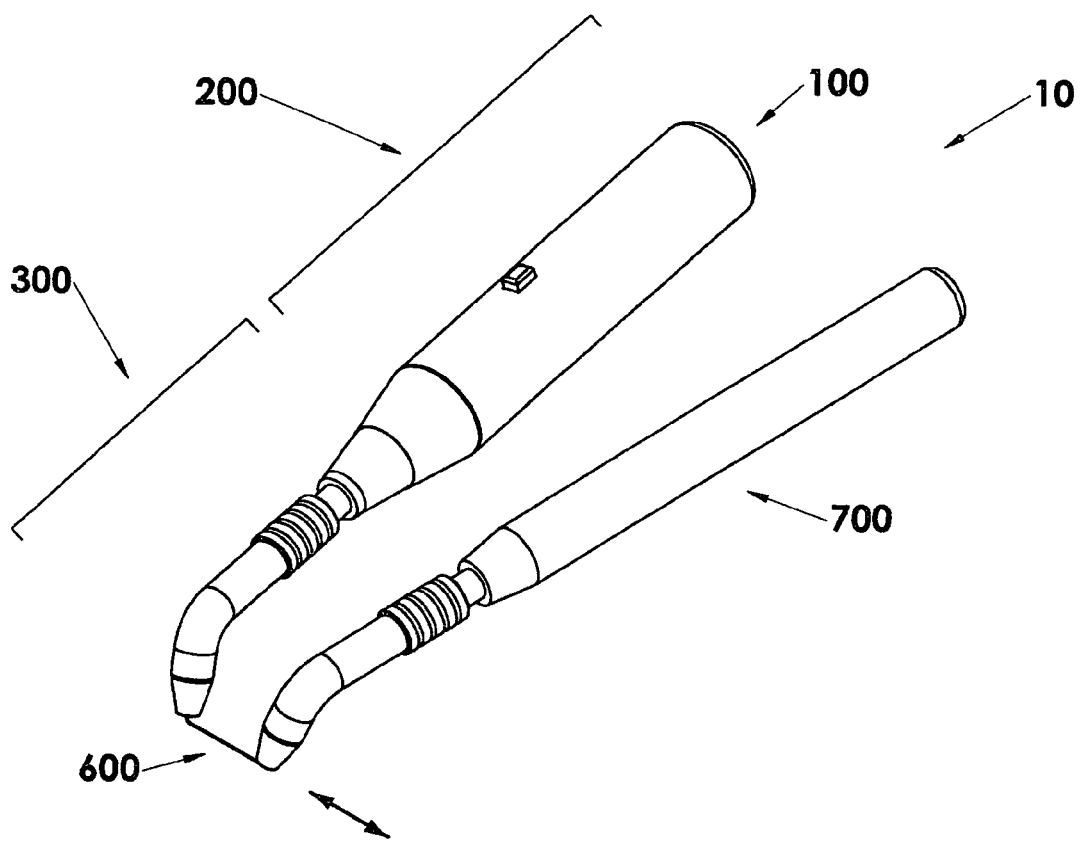
FIG. 1A is a perspective view of the electric flossing apparatus in accordance with a first embodiment of the present invention.
Figure 1B:
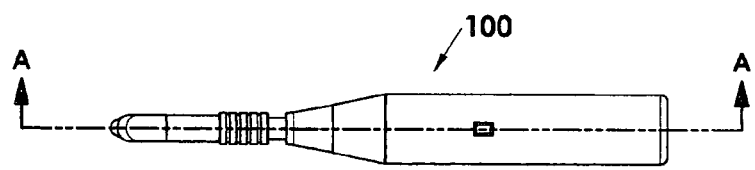
FIG. 1B is a plan view of the drive unit and flossing head in accordance with a first embodiment of the present invention.

A preferred embodiment of the electric dental flosser of the present invention is shown generally as 10 in FIG. 1A. The flosser 10 generally includes a powered unit 100 (e.g., a first handle), a non-powered unit 700 (e.g., a second handle), and a disposable floss assembly 600. Further, the powered unit 100 is comprised of a power or drive unit 200 and a flossing head 300.

Figure 2A:
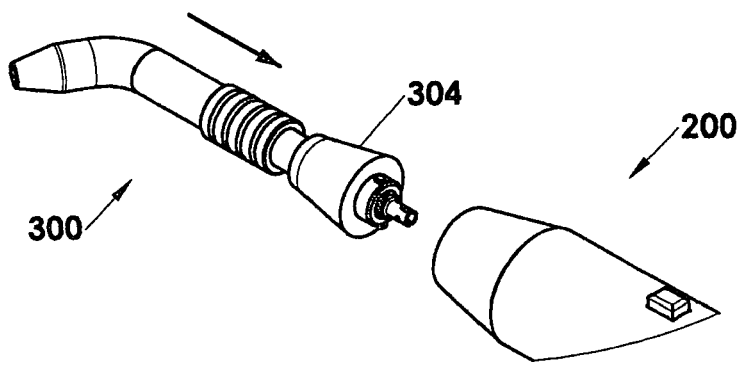
FIG. 2A is a fragmentary perspective view showing the flossing head and drive unit prior to connection.
Figure 2B:
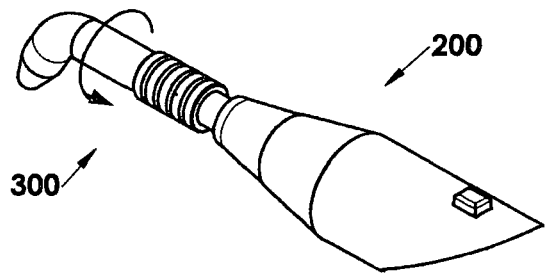
FIG. 2B is a fragmentary perspective view showing the flossing head and drive unit after connection.
Figure 2C:
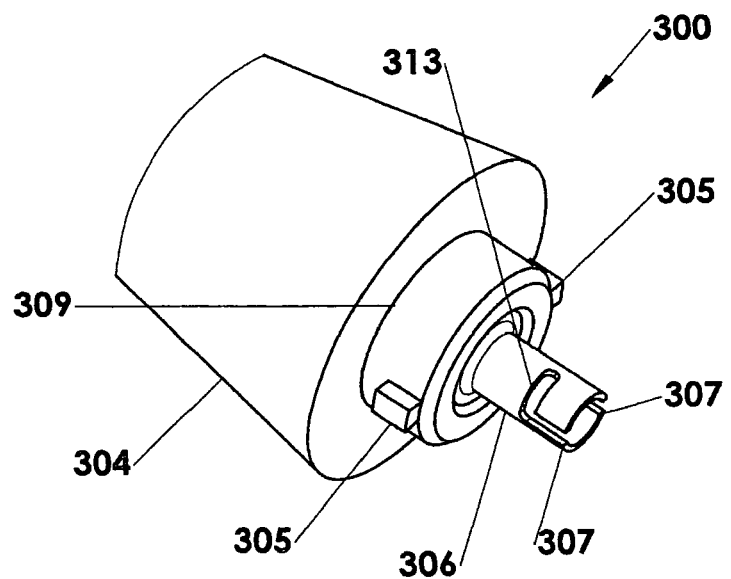
FIG. 2C is a fragmentary perspective view showing the connecting features of the flossing head.

As shown in FIGS. 2A, 2B and 2C the electric flosser 10 includes a drive unit 200 which is detachably connected to the flossing head 300. The drive unit 200 may be in the form of that which is used with a commercially available powered toothbrush. The flossing head 300 would simply replace the toothbrush attachment in this case. In any case, to connect the flossing head 300 to the drive unit 200, the user aligns cylindrical feature 309 with bore 292 in drive unit 200, while simultaneously aligning the small projections 305 with the top of the L-shaped grooves 290 in the drive unit 200 (best seen in FIG. 3B). The user pushes or presses the head 300 down so that the small projections 305 contact a bottom surface 291 of the L-shaped grooves 290. When the small projections 305 have contacted the bottom surface 291, the user then turns the head 300 approximately 90 degrees with respect to the drive unit 200 to lock the flossing head 300 into place. During this longitudinal translation and approximate 90 degree rotation, L-shaped slots 307 in drive shaft 306 additionally detachably connect drive shaft 306 of flossing head 300 to the output shaft 212 of drive unit 200. Any way of detachably interconnecting the drive unit 200 and flossing head 300 may be utilized.

Figure 3A:
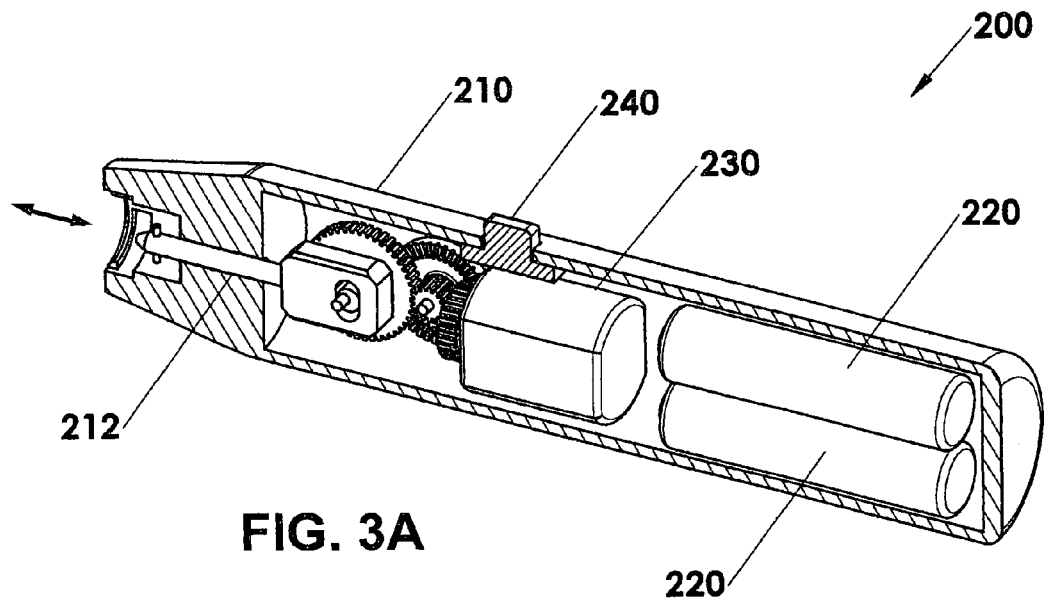
FIG. 3A is a cross-sectional perspective view of the drive unit taken along line A-A in FIG. 1B.
Figure 3B:
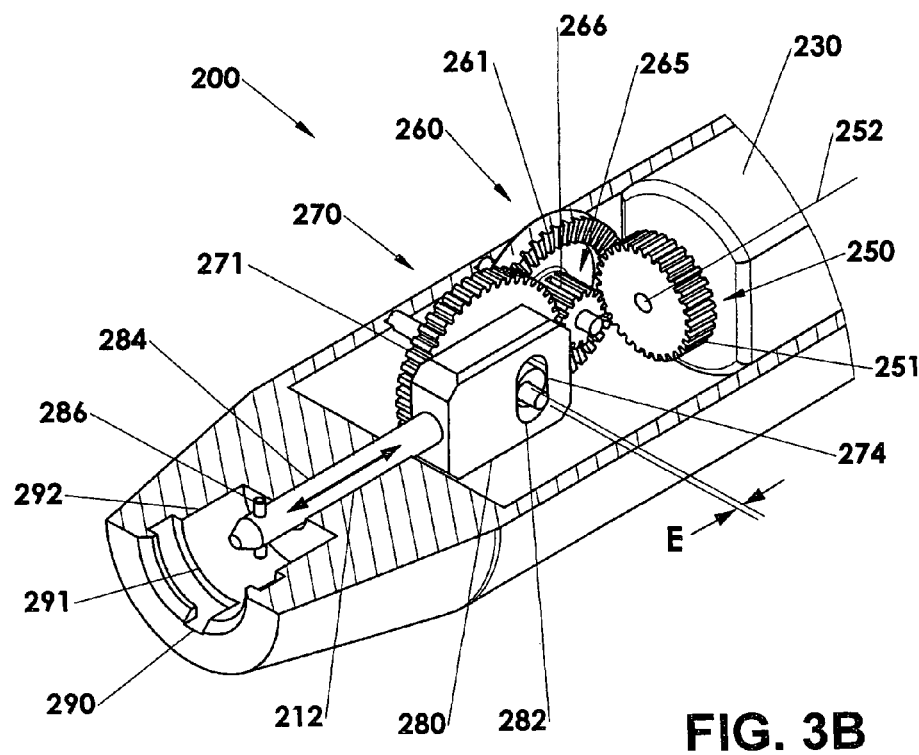
FIG. 3B is a fragmentary cross-sectional perspective view of the drive unit taken along line B-B in FIG. 1C.

Referring now to FIG. 3A, the drive unit 200 includes a hollow structure 210 that a user may grasp to manipulate the flossing head 300. Structure 210 houses a drive motor 230 and a battery unit 220. The battery unit 220 is electrically connected to the motor 230. This electrical connection includes on-off switch 240. Referring to FIG. 3B, the embodiment further includes a first gear 250 which is operatively connected to and powered by the motor 230. The first gear 250 rotates about the longitudinal axis 252. A second crown gear 260 is operably connected to the first gear 250. The second gear 260 rotates about an axis approximately normal to axis 252 of gear 250. Teeth 251 of the first gear 250 mesh with teeth 261 of the second gear 260, thus causing second gear 260 to rotate when first gear 250 rotates. Third gear 265 is fixably connected to second gear 260 and rotates with second gear 260 about the same axis as gear 260. A fourth gear 270 is operably connected to third gear 265. Teeth 266 of gear 265 mesh with teeth 271 of gear 270, so causing fourth gear 270 to rotate when third gear 265 rotates. Thus, fourth gear 270 rotates when the motor 230 is connected to battery unit 220 thru switch 240.

Cylindrical feature 274 is fixably connected to gear 270. The axis of eccentric cylindrical feature 274 is aligned parallel to the rotational axis of fourth gear 270 and is offset radially by a distance denoted by the letter E. Cylindrical feature 274 is operably connected to scotch yoke 280 thru the action of slot 282. Output shaft 212 is fixably connected to scotch yoke 280 and is supported by cylindrical guide bearing 284, which allows shaft 212 and scotch yoke 280 to axially reciprocate in the direction of the double headed arrow by a distance equal to twice the eccentricity E. Pin 286 is fixably attached to the end of the output shaft 284, and in conjunction with L-shaped groove 290 is used to connect the drive unit 200 to the flossing head 300. The clocking of output shaft 284 as well as pin 286 with respect to the L-shaped groove 290 is maintained by the close clearance between the mating faces of the scotch yoke 280 and fourth gear 270. Finally, it should be noted that the eccentricity E as well as the gear teeth ratios between gears 250 and 260, and between gears 265 and 270 may be adjusted to optimize the maximum force imparted to the floss assembly 600, as well as the stroke and reciprocation frequency of the floss assembly 600. This optimization would be based on ease of use, safety of use, and cleaning efficiency.

Figure 4A:
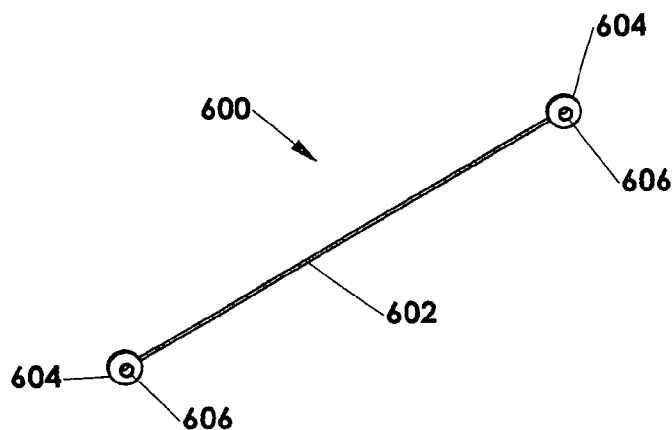
FIG. 4A is a perspective view of the first embodiment of the floss assembly.
Figure 4B:
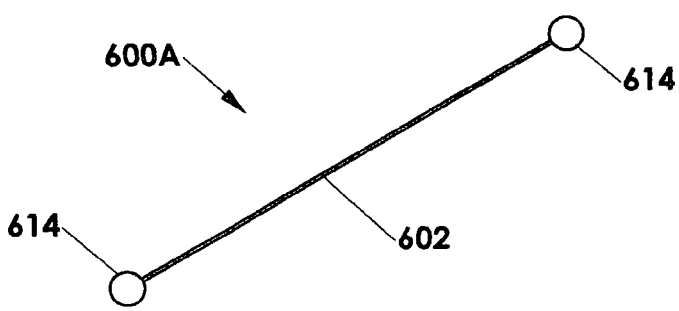
FIG. 4B is a perspective view of the second embodiment of the floss assembly.
Figure 4C:
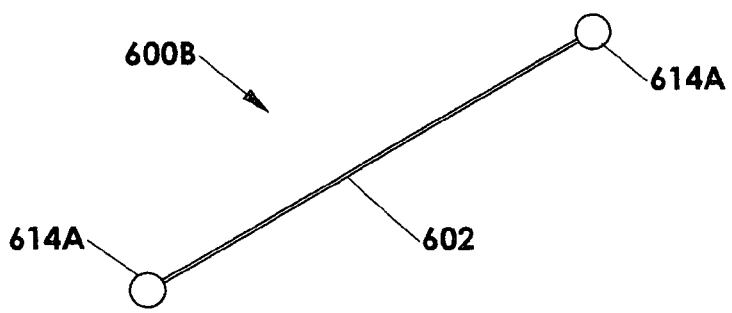
FIG. 4C is a perspective view of the third embodiment of the floss assembly.
Figure 4D:
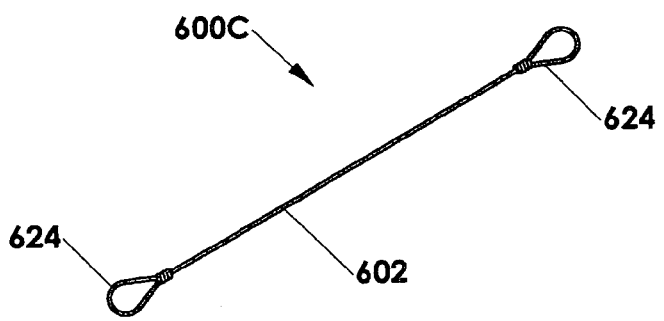
FIG. 4D is a perspective view of the fourth embodiment of the floss assembly.

As shown in FIG. 4A, the first embodiment of the floss assembly 600 consists of a short length of dental floss 602 approximately 0.75 to 1.5 inch long in one embodiment. Attached at each end of floss 602 is a small plastic bead 604 with a central thru hole 606. The bead 604 is approximately 0.050 to 0.125 inch in diameter in one embodiment. The dental floss 602 may be simply tied to the beads 604 or the beads 604 may be injection molded onto the floss 602 with suitable measures to insure a strong connection, such as molding the bead 606 around a knot or loop of floss 602 tied into the ends of the floss 602. FIGS. 4B, 4C and 4D present second third and fourth embodiments of the floss assembly 600 which will be more fully described later.

Figure 5A:
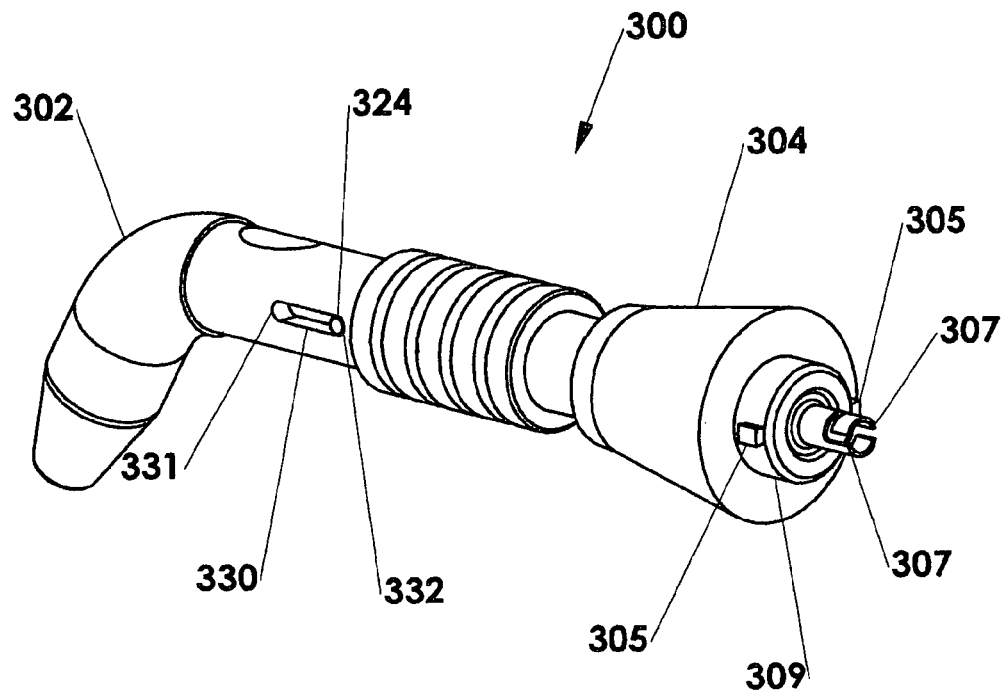
FIG. 5A is a perspective view of the first embodiment of the flossing head.
Figure 5B:
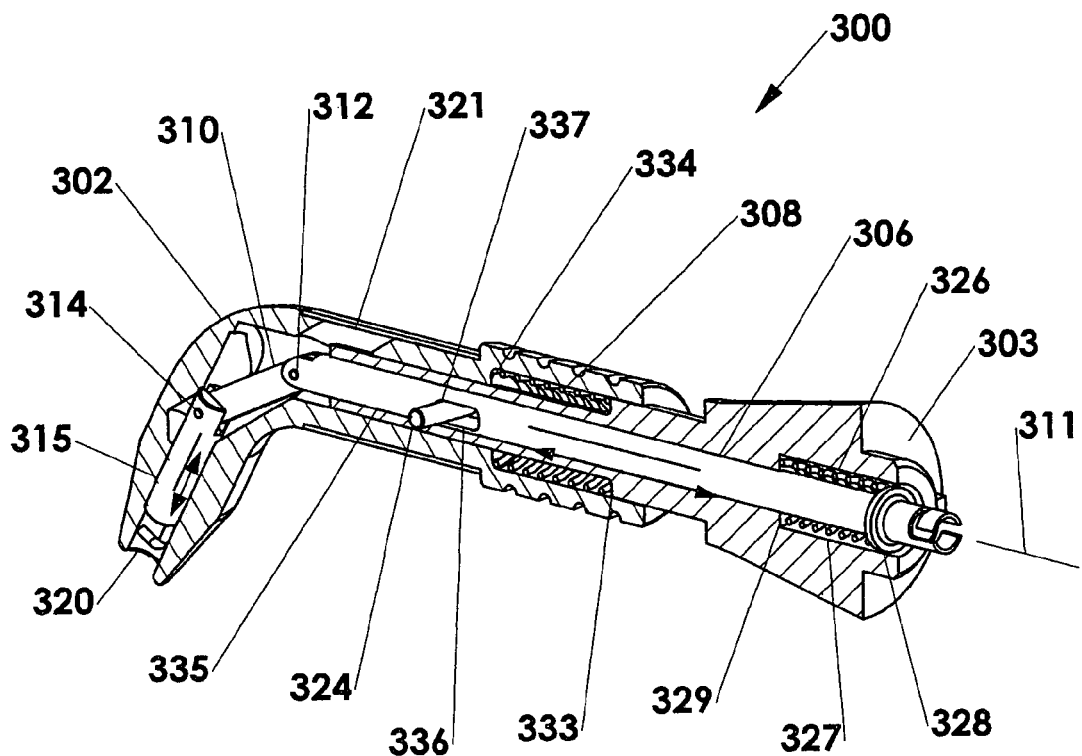
FIG. 5B is a cross-sectional perspective view of the first embodiment of the flossing head taken along line A-A of FIG. 1B. This figure shows the first embodiment of the drive linkage in the latched position.

FIGS. 5A and 5B present a perspective view and cross-section perspective view of a first embodiment of angled flossing head 300. The stationary portion 304 of flossing head 300 attaches to drive unit 200 thru use of latching projections 305 and cylindrical feature 309 previously described. Stationary portion 304 has a central bearing surface 335 along longitudinal axis 311 which serves as a support and linear guide for drive shaft 306 that axially reciprocates during operation of motor 230. L-shaped slots 307 (best seen in FIG. 2C) in the end of drive shaft 306 engage with pin 286 of drive unit 200 to detachably interconnect flossing head 300 with drive unit 200. Spring 326 in bore 327 of stationary portion 304 pushes against flange 328 of drive shaft 306. Thus, spring 326 urges drive shaft 306 towards end 303 of stationary portion 304. Drive shaft 306 is prevented from traveling further towards end 303 by pin 324 coming into contact with end 337 of slot 336 in drive shaft 306. A second function of pin 324 is to prevent rotation about longitudinal axis 311 of drive shaft 306 with respect to stationary portion 304. During attachment of flossing head 300 to drive unit 200, pin 324 guarantees that the L-shaped slots 307 in drive shaft 306 remain aligned with pins 305. This in turn insures that, as pins 305 enter the L-shaped groove 290 in drive unit 200, the pin 286 in output shaft 284 enters the L-shaped slots 307 in the drive shaft 306 of the flossing head 300. The purpose of spring 308 is to guarantee that the bottom 313 (shown in FIG. 2C) of L-shaped slots 307 bottom out against pin 284 prior to projections 305 contacting the bottom surface 291 of groove 290. After projections 305 reach the surface 291, the user rotates flossing head 300 approximately 90 degrees to lock the head 300 in place. During this approximately 90 degree rotation, the pin 284 also locks into the L-shaped slots 307 in the drive shaft 306, thus simultaneously connecting the output shaft 284 of the drive unit 200 to the drive shaft 306 of the flossing head 300. When this connection is complete, the flossing head drive shaft 306 will axially reciprocate whenever the drive unit output shaft 284 axially reciprocates. It will be recognized by those skilled in the art to which the present invention pertains, that alternate means of simultaneously connecting the output shaft 284 of drive unit 200 to the drive shaft 306 of flossing head 300 are possible. Any appropriate way of interconnecting drive unit output shaft 284 with flossing head drive shaft 306 to axially reciprocate the drive shaft 306 during operation of motor 230 may be utilized.

Figure 1C:
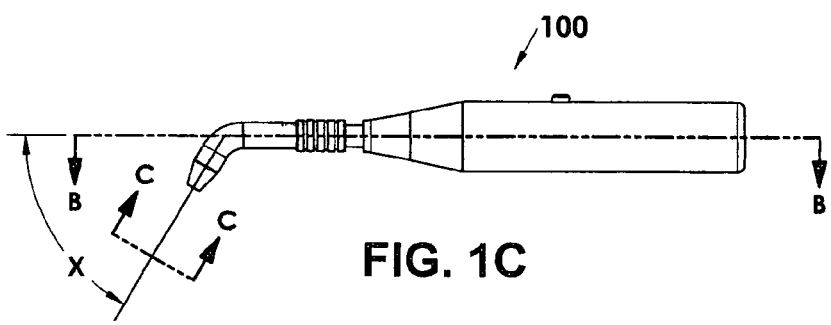
FIG. 1C is an elevation view of the drive unit and flossing head in accordance with a first embodiment of the present invention.

Continuing with FIGS. 5A and B, the flossing head 300 has an outer moving portion 302, hereafter called the angled flosser tip 302. The distal end of flosser tip 302 is angled for ease of use during flossing. This angled portion is within a single dimension or reference plane (e.g., a single reference plane would contain a control axis of the entire flossing head 300 and drive unit 200). The angle "X" as shown in FIG. 1C can be varied between approximately zero degrees and 90 degrees. In the case of a zero degree tip angle, the drive mechanism is simplified. The zero degree or straight flosser head 500 will be described in a later paragraph. Now, continuing with the description of angled flossing head 300, the slot ends 331 and 332 of slot 330 (FIG. 5A) in conjunction with pin 324 control the axial travel of angled tip 302 with respect to stationary portion 304. Spring 308, acting between surface 333 of stationary portion 304 and surface 334 of tip 302, urges the end 332 of slot 330 against pin 324.

Figure 5C:
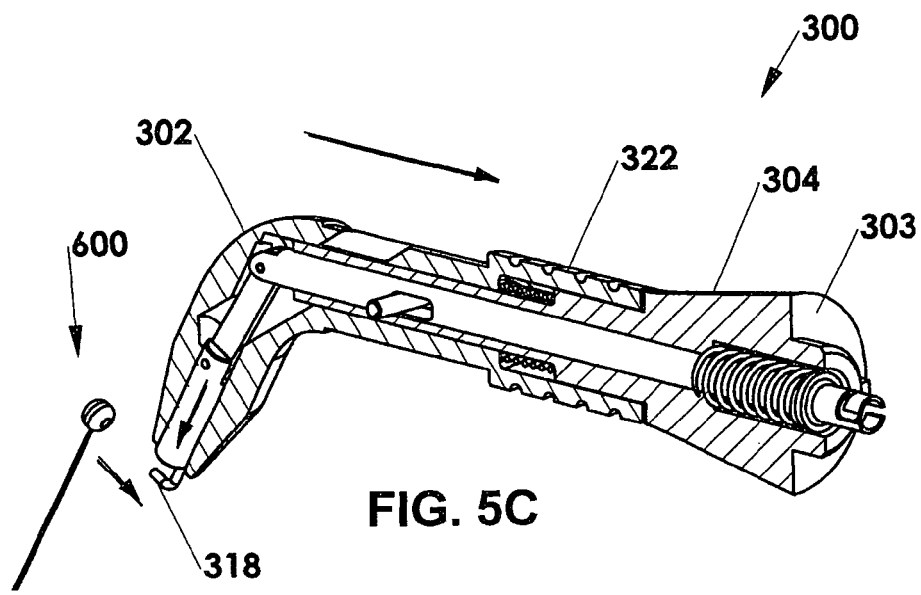
FIG. 5C is a cross-sectional perspective view of the first embodiment of the flossing head taken along line A-A of FIG. 1B. This figure shows the first embodiment of the drive linkage in the unlatched position with a first embodiment of the floss assembly prior to attachment.
Figure 5D:
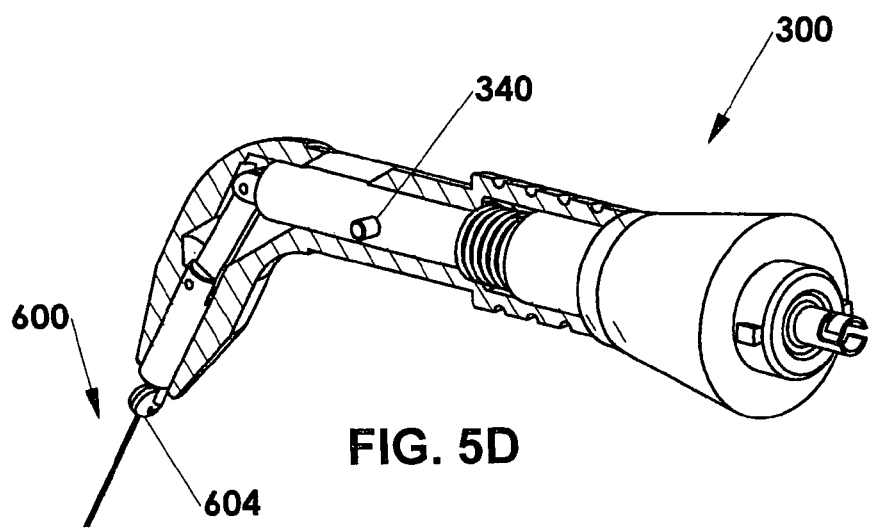
FIG. 5D is a cross-sectional perspective view of the first embodiment of the flossing head taken along line A-A of FIG. 1B. This figure shows the first embodiment of the drive linkage in the unlatched position and with a first embodiment of the floss assembly being attached.
Figure 5E:
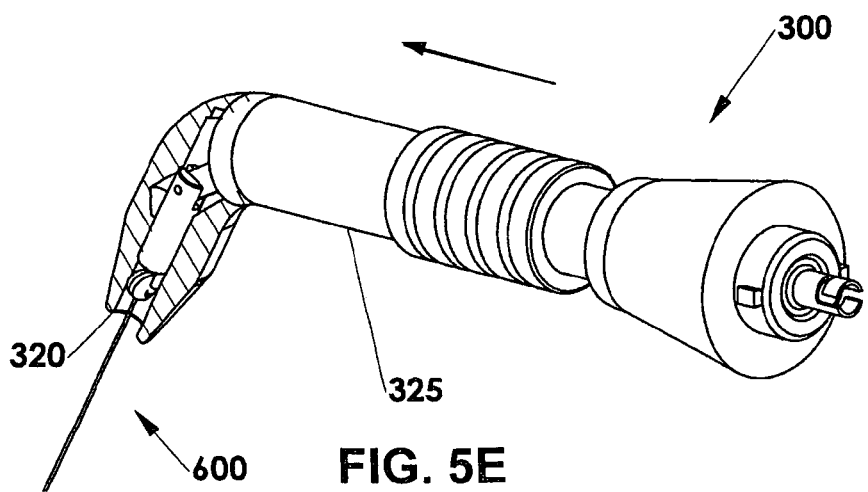
FIG. 5E is a fragmentary cross-sectional perspective view of the first embodiment of the flossing head taken along line A-A of FIG. 1B. This figure shows the first embodiment of the drive linkage in the latched position and with a first embodiment of the floss assembly fully attached.

Drive shaft 306 is rotatively connected to link 310 by pin 312. Link 310 is additionally rotatively connected to floss connection fitting 315 by pin 314. Floss connection fitting 315 is guided axially by bore 320 in tip 302. Bore 321 provides clearance for motion of link 310 during axial reciprocation of drive shaft 306 while flossing, as well as during retraction of tip 302 for floss attachment as shown in FIGS. 5C thru 5E. Bore 321, as well as slot 330, are closed by sleeve 325 which may be a heat shrink material. Alternately, tip 302 may be fabricated as mirror image halves with the necessary internal guide bores, slots and clearances, but without external openings. These angled tip halves would be fastened together during assembly and would eliminate the need for sleeve 345.

In order to attach floss assembly 600, as shown by FIG. 5C, the user retracts tip 302 axially towards end 303 of stationary portion 304. In so doing, floss attachment hook 318 is axially translated outside of tip 302 (e.g., becomes "exposed") by action of connecting link 310. This manual retraction is aided by finger traction grooves 322. This retraction is opposed by spring 308 which maintains the tip 302 in the latched position when it is manually released by the user.

Referring now to FIGS. 5C, 5D, and 5E, floss assembly 600 is shown being attached (e.g., detachably coupled) to the flossing head 300 by the insertion of L-shaped hook 318 (a fitting) through hole 606 of bead 604 (another fitting). FIG. 5E shows how bead 604 and a portion of the floss 602 are captured in bore 320 of tip 302 after the tip 302 is manually released. The double headed arrows in FIG. 6A further show how the axial reciprocating motion of drive shaft 306 is communicated to the floss connection fitting 315 by link 310. Notably, the attachment hook 318 and its corresponding bead 604 each remain within the tip 302 at this time (e.g., remain within bore 320). That is, the detachably coupled attachment hook 318 and bead 604 axially reciprocate within the flossing head 300 during operation of the drive motor 230. This thereby shields these moving parts from the user's tissue during flossing operations.

Figure 6A:
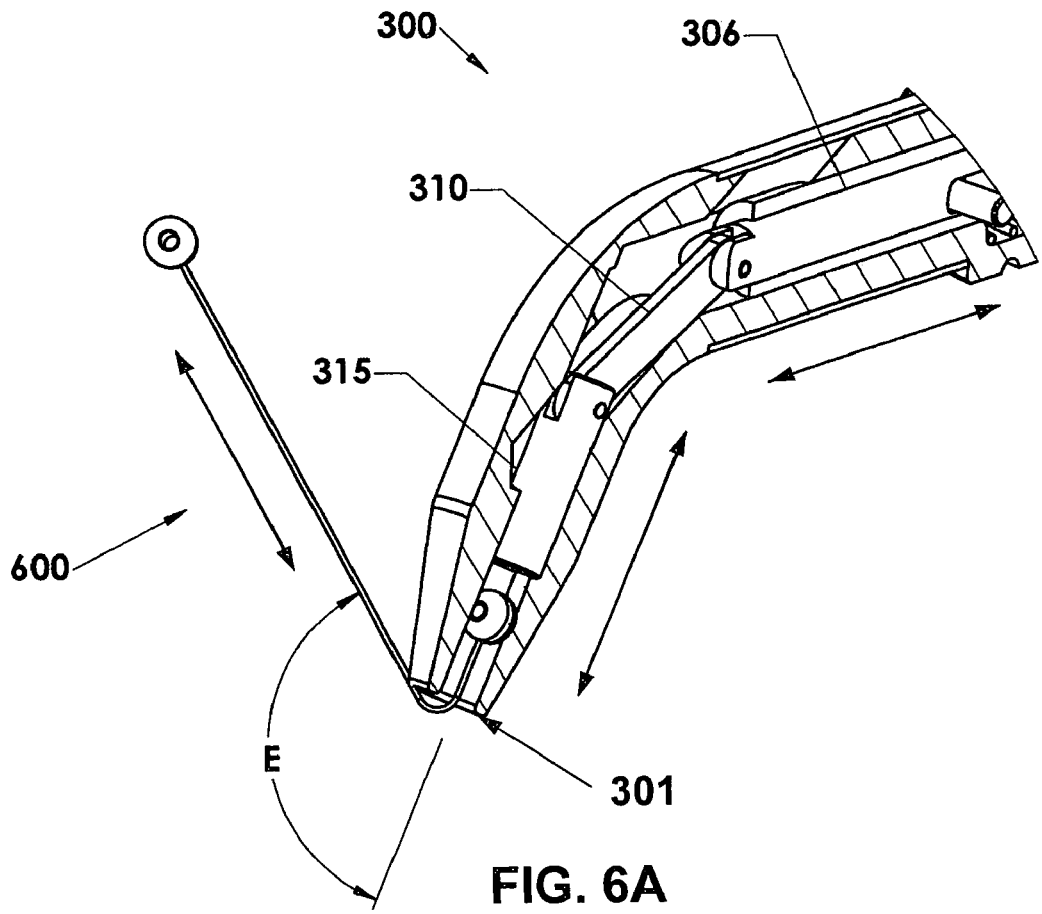
FIG. 6A is a fragmentary cross-sectional perspective view of an embodiment of the flossing head showing the motion imparted to the floss. The view is taken along line A-A of FIG. 1B.
Figure 6B:
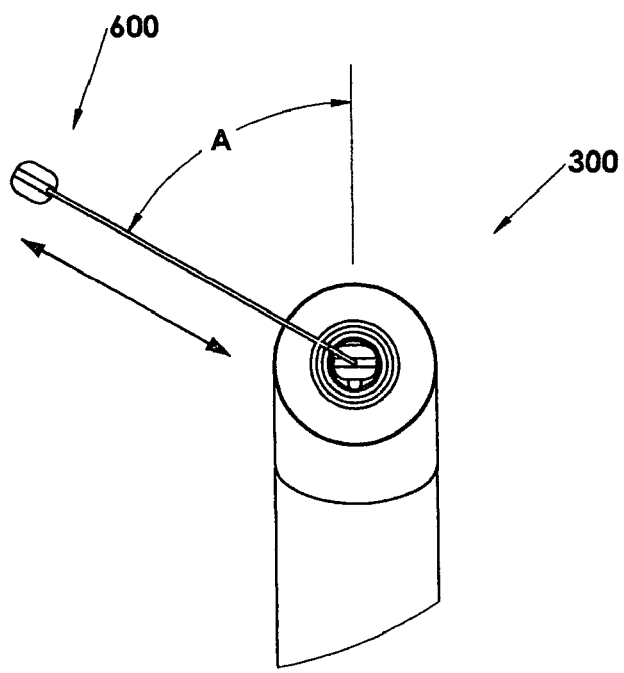
FIG. 6B is a fragmentary end view of an embodiment of the flossing head tip showing the exit of the floss from the flossing head. The view is taken along line C-C of FIG. 1C.

FIGS. 6A and 6B further show that, with the floss assembly 600 being stretched tight, the axial reciprocating motion of the drive shaft 306 is imparted to the full length of floss 602, regardless of the azimuth and elevation angles "A" and "E" which the floss 602 departs from lip 301 of tip 302 of flossing head 300. The floss 602 extends within the bore 320, which has a closed perimeter. Therefore, the floss 602 may be supported by the sidewall that defines the bore 320, regardless of where the floss 602 is contacting the sidewall that defines the bore 320.

Figure 7A:
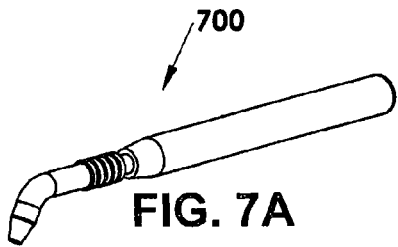
FIG. 7A is a perspective view of the first embodiment of the non-powered floss handle.

A first embodiment of the non-powered flossing unit 700, as shown in FIG. 7A, will now be described. It should be noted that non-powered unit 700 is very similar to the first embodiment of the flossing head 300. The last two digits of the numbering system will reflect this similarity; thus spring 708 performs the same function as spring 308 in flossing head 300.

Figure 7B:
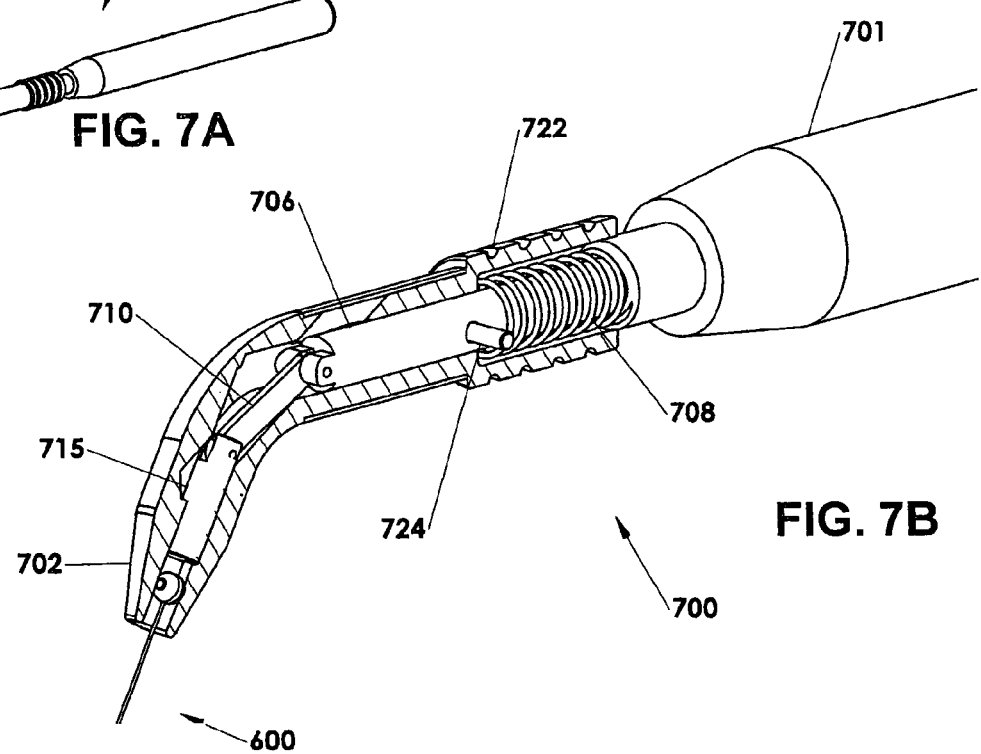
FIG. 7B is a fragmentary partial cross-sectional perspective view of the first embodiment of the non-powered floss handle with the first embodiment of the floss connection link and the first embodiment of the floss assembly attached.

Referring now to FIG. 7B, drive shaft 706 is fixably attached to handle 701. The flossing unit 700 is non-powered so drive shaft 706 functions more as an anchor in this case, and is not driven by a motor or the like to impart motion to the floss 602. Drive shaft 706 is rotatively connected to link 710, which is in turn rotatively connected to connection member 715. Spring 708 holds the axially movable angled tip 702 in the latched configuration except when manually retracted by the user to install the floss assembly 600. The attachment of the floss assembly 600 is identical to that of the other end of the floss 602 to the flossing head 300 as shown in FIGS. 5C, 5D, and 5E.

Figure 9A:
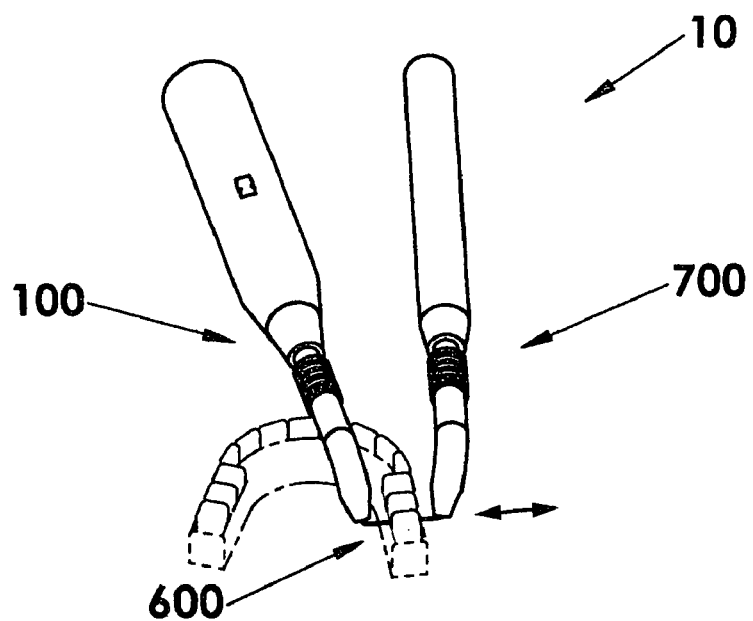
FIG. 9A is a perspective view of the electric flossing apparatus of FIG. 1A with the floss pulled tight for insertion between two teeth.
Figures 9B, 9C:
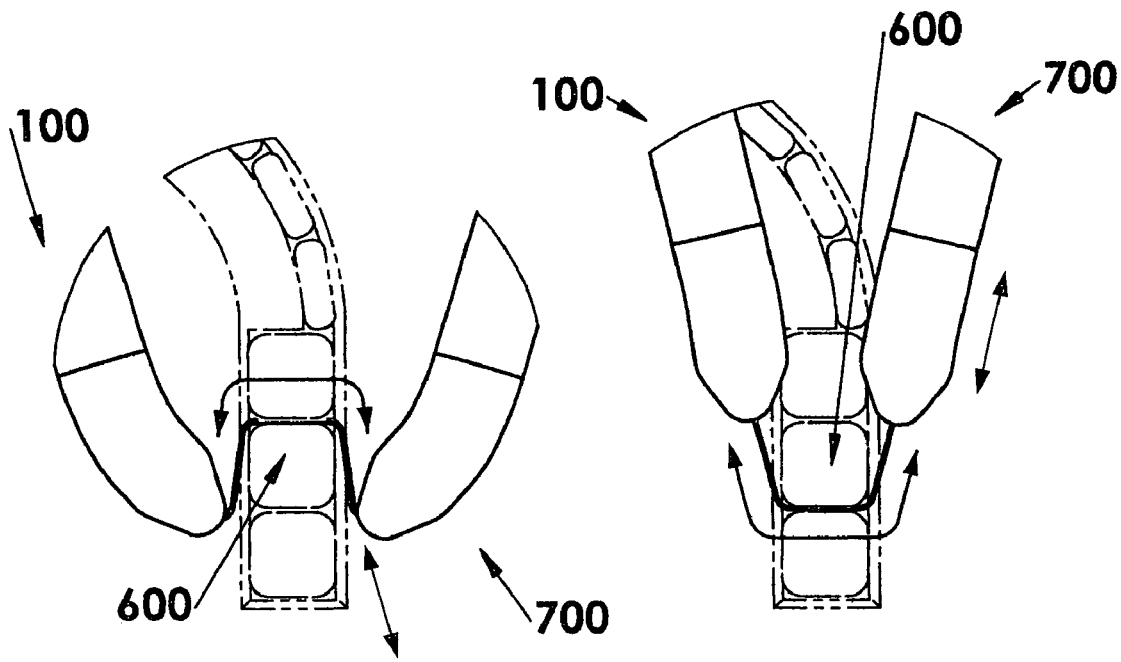
FIG. 9B is a fragmentary perspective view of the electric flossing apparatus of FIG. 1A with the floss wrapping around the front and sides of a tooth.
FIG. 9C is a fragmentary perspective view of the electric flossing apparatus of FIG. 1A with the floss wrapping around the back and sides of a tooth.

FIG. 9A shows the assembled flosser 10 being inserted between two teeth by the user. As shown, the two-handed operation allows the user to pull the floss 602 tight for easy insertion between the teeth. The two-headed arrow shows the general reciprocating motion of the floss 602 which not only aids in cleaning, but also helps with the insertion of floss 602 between tightly spaced teeth. This is accomplished by orienting the friction vector opposing floss velocity generally in the direction of the relatively high speed reciprocating motion, as indicated by the two-headed arrow, rather than opposing the much slower velocity of the floss 602 in the direction perpendicular to the two-headed arrow or towards the gum line during insertion between the teeth. FIGS. 9B and 9C show how the two-handed operation allows the floss 602 to be alternately wrapped around the fronts and backs, as well as the corners and sides of all teeth during flossing. These figures also show how the reciprocating motion of the floss 602 is maintained regardless of the direction that the floss 602 departs the tip 302 of the flossing head 300 or the shape of the path it takes.

Any appropriate way of detachably coupling the floss assembly 600 with each of the non-powered flossing unit 700 and powered unit 100 may be utilized. Representative alternate embodiments 600A, 600B and 600C of floss assembly 600 are shown in FIGS. 4B, 4C and 4D. These embodiments require modifications to flossing head 300 which are designated as 300A, 300B, 300BB and 300C and shown in FIGS. 10A, 10B, 10C, and FIGS. 15A and 15B. There are a number of features common to all of these variations, as well as to floss assembly 600. One is that the coupling of the dental floss assembly to each of the powered unit and non-powered unit of the flosser remains recessed within or within the interior of the respective unit during flossing operations. Another is that the fitting used by both the powered and non-powered unit of the flosser may "move" from this recessed position to an exposed position to allow for the fitting to be coupled with or decoupled from a corresponding fitting of the dental floss assembly.

Figure 10A:
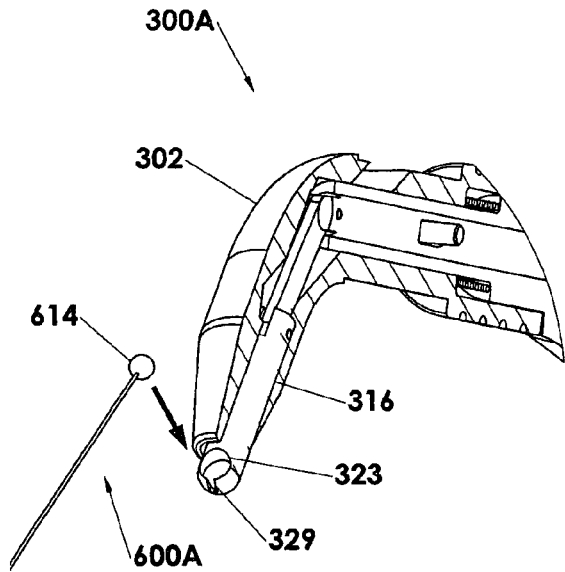
FIG. 10A is a fragmentary cross-sectional perspective view of the second embodiment of the flossing head floss connection link in the unlatched position prior to the attachment of the second embodiment of the floss assembly. The view is taken along line A-A of FIG. 1B.
Figure 10B:
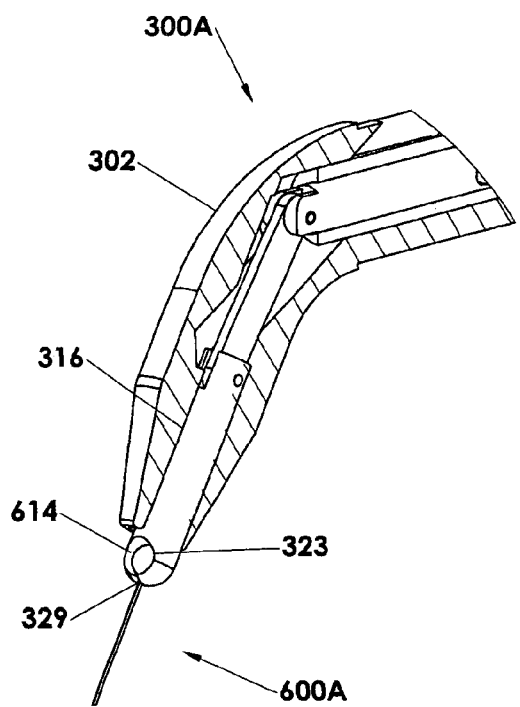
FIG. 10B is a fragmentary cross-sectional perspective view of the second embodiment of the flossing head floss connection link in the unlatched position with the second embodiment of the floss assembly in the attachment socket. The view is taken along line A-A of FIG. 1B.

Floss assembly 600A (FIG. 4B) is identical to floss assembly 600, except that plastic beads 604 are replaced by plastic balls 614, with no hole extending therethrough. As shown in FIGS. 10A and 10B, plastic ball 614 of floss assembly 600A is inserted into socket 323 of floss connection fitting 316. Socket 323 has a slot 329 which allows the floss 602 to exit the socket 323. Embodiment 300A is identical to embodiment 300 of the flossing head, except that floss connection link 315 has been replaced by link 316 which incorporates socket 323 and slot 329.

Figure 10C:
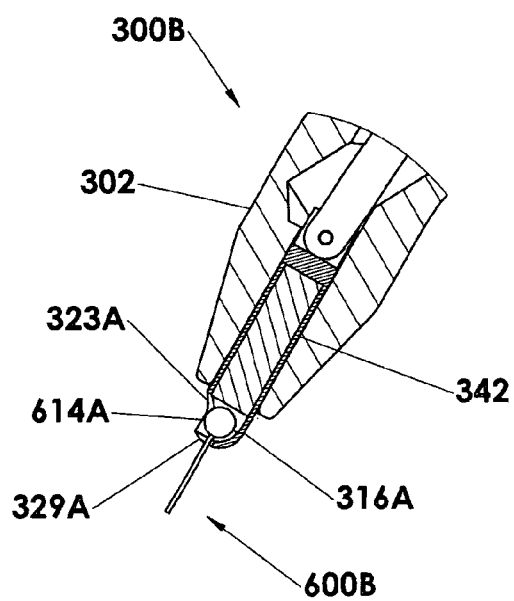
FIG. 10C is a fragmentary cross-sectional elevation view of the third embodiment of the flossing head magnetic floss connection link, showing the attachment of the third embodiment of the floss assembly. The view is taken along line A-A of FIG. 1B.

Floss assembly 600B (FIG. 4C) is identical to floss assembly 600A, except that plastic beads 614 are replaced by metal balls 614A, with no hole extending therethrough. The balls 614A are made of a material such as iron which is subject to magnetic attraction. The balls 614A would be crimped, tied or otherwise fastened onto the dental floss 602 and covered with a protective coating to prevent corrosion. As shown in FIG. 10C, metal ball 614A of floss assembly 600B is inserted into socket 323A of floss connection fitting 316A. Socket 323A has a slot 329A which allows the floss 602 to exit the socket 350A. Embodiment 300B is identical to embodiment 300A of the flossing head, except that floss connection link 316 has been replaced by link 316A which has a central bore to which magnet 342 is fixably attached. Magnet 342 is located in link 316A such that it forms one end of socket 323A. The end of magnet 342 may be shaped in either a flat or in a somewhat concave fashion to more naturally form the end of socket 323A. The purpose of magnet 342 is to aid in attaching floss assembly 600B by using the magnetic attraction between ball 614A and magnet 342 to guide the ball 614A into the socket 323A and hold it there while the tip 302 is being manually released by the user to capture the floss assembly 600B.

Figure 15A:
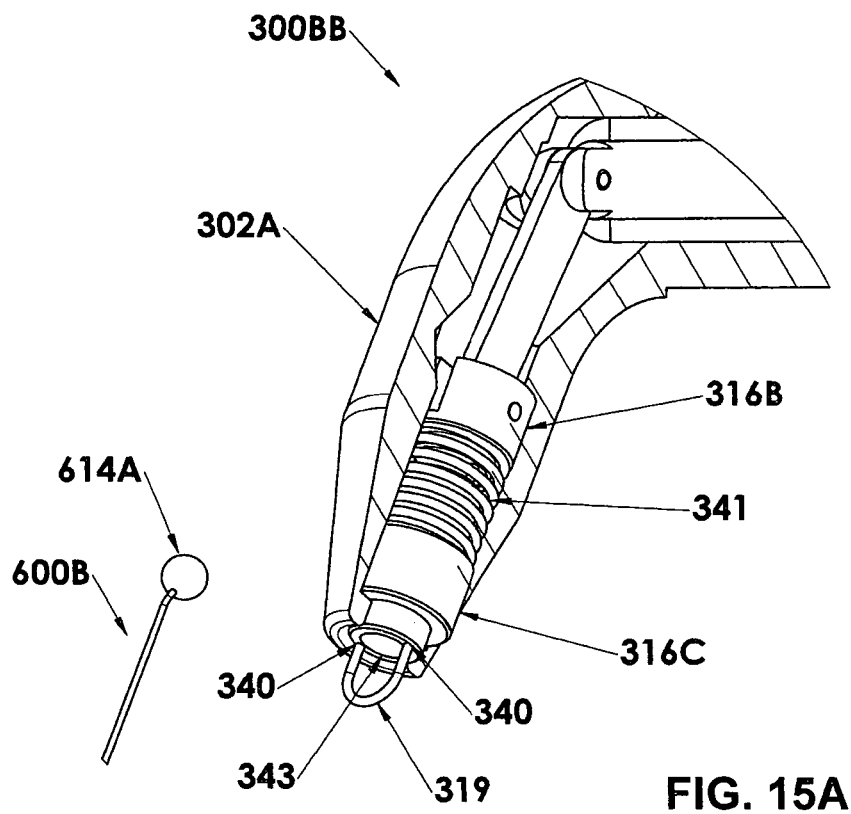
FIG. 15A is a fragmentary cross-sectional perspective of a fifth embodiment of the flossing head floss connection link showing the third embodiment of the floss assembly attached. The view is taken along line A-A of FIG. 1B.
Figure 15B:
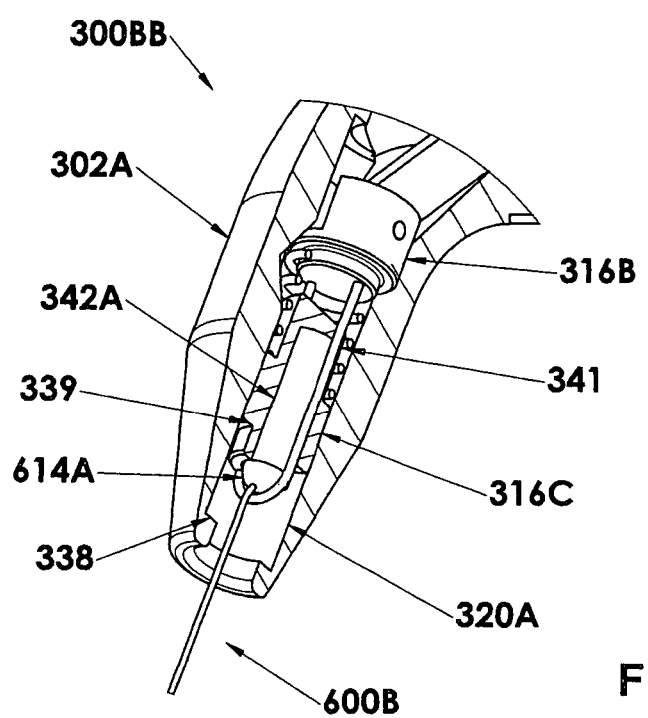
FIG. 15B is a fragmentary cross-sectional perspective of a fifth embodiment of the flossing head floss connection link showing attachment of the third embodiment of the floss assembly. The view is taken along line A-A of FIG. 1B.

FIGS. 15A and 15B present an additional embodiment of the flossing head designated as 300BB. This embodiment also uses magnetic attraction to aid in the attachment of floss assembly 600B. The essential difference in this embodiment it that it employs a U-shaped jaw 319 to capture and latch floss assembly ball 614A against magnet 342A. U-shaped jaw 319 is fixably attached to connection link portion 316B. U-shaped jaw 319 would be fabricated from a non-magnetic stainless steel wire such that it would not interfere with the attractive force between magnet 342A and ball 614A. In this embodiment, link 316A is split into two link portions 316B and 316C. Link portion 316C has a central socket to which magnet 342A is fixably attached, as well as two parallel thru holes 340 thru which the legs of U-shaped jaw 319 pass. There is radial clearance in thru holes 340 which allow link component 316C to translate axially relative to link component 316B. Link components 316B and 316C are biased apart by the force of spring 341. The purpose of spring 341 is to clamp ball 614A between spherical socket 343 in the end of magnet 342A and U-shaped jaw 319, as best shown in FIG. 15B. FIG. 15A demonstrates how surface 338 in tip 302A stops the axial travel of link portion 316C when surface 339 of link component 316C contacts it as the user manually retracts tip 302A for floss attachment or release. After travel of link component 316C is terminated, link component 316B travels a small additional amount as the user completes the retraction of the movable flosser tip 302A. This final motion further compresses spring 341, and increases the distance or opening between the U-shaped jaw 319 and the spherical socket 343 in the end of magnet 342A a sufficient amount to easily allow the release or insertion of ball 614A.

Figure 10D:
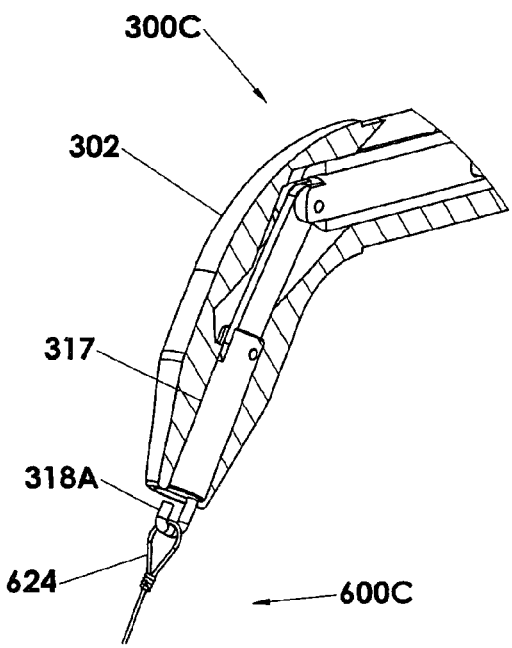
FIG. 10D is a fragmentary cross-sectional elevation view of the fourth embodiment of the flossing head floss connection link, showing the attachment of the fourth embodiment of the floss assembly. The view is taken along line A-A of FIG. 1B.

Floss assembly 600C (FIG. 4D) simply has loops tied into each end of floss 602. These loops 624 engage with hooks 318A of floss connection fitting 317 as shown in FIG. 10D. Embodiment 300C of the flossing head is identical to embodiment 300, except that flossing attachment fitting 315 has been replaced with fitting 317 to which J-shaped hook 318A is fixably attached.

Figure 11A:
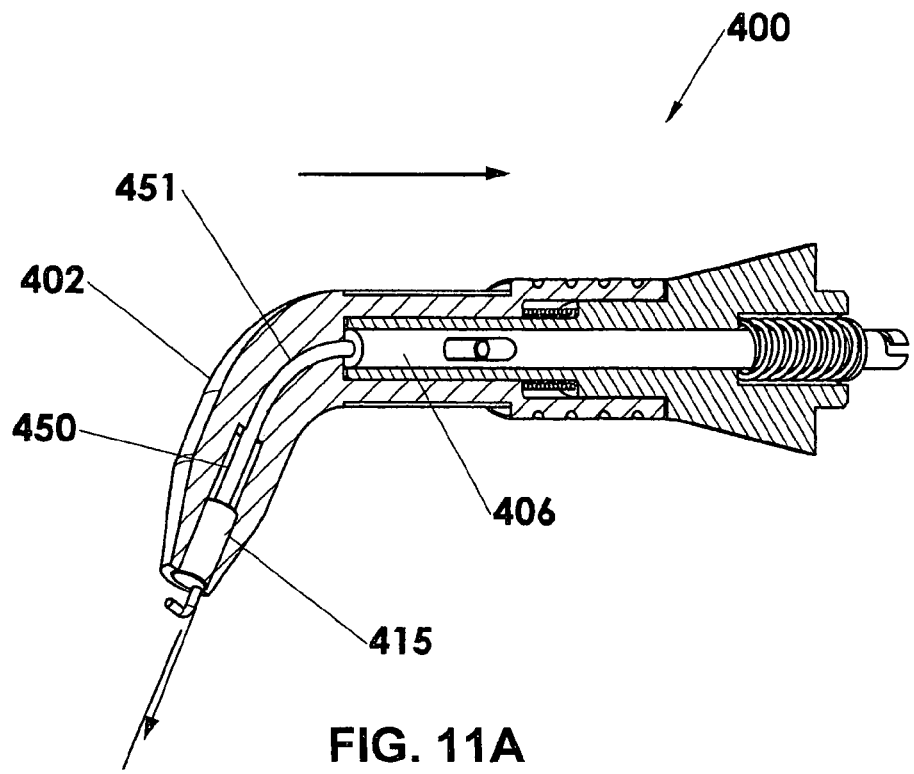
FIG. 11A is a cross-sectional perspective view of the first embodiment of the flossing head assembly with the second embodiment of the drive linkage in the unlatched position. The view is taken along line A-A of FIG. 1B.
Figure 11B:
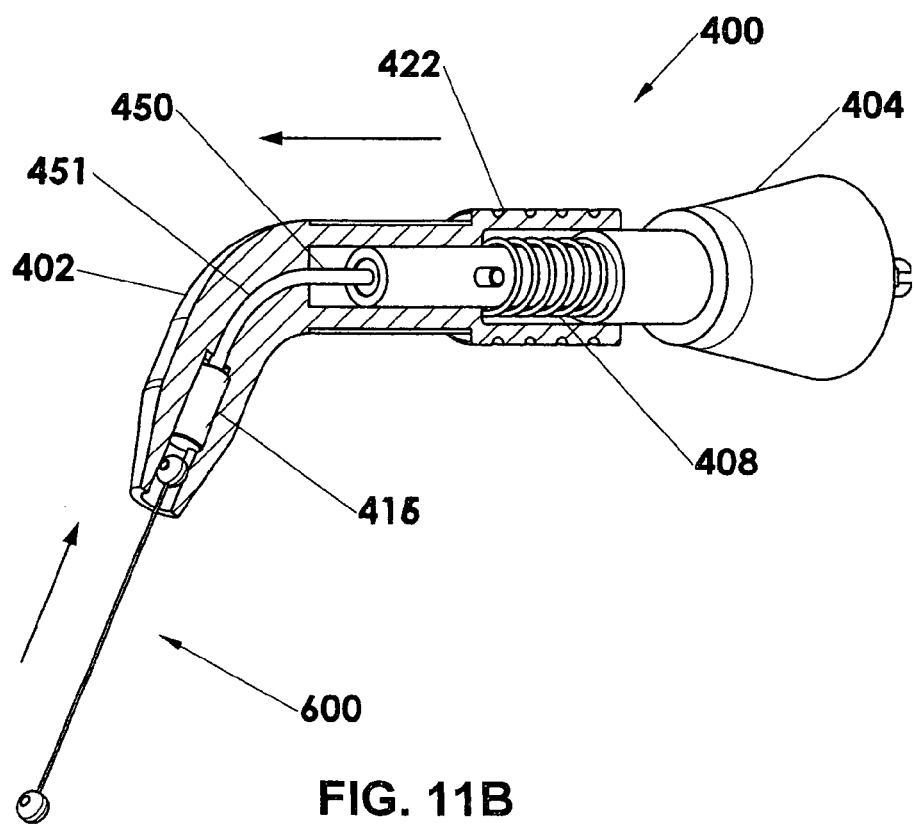
FIG. 11B is a cross-sectional perspective view of the first embodiment of the flossing head assembly with the second embodiment of the drive linkage in the latched position. The view is taken along line A-A of FIG. 1B.

Further embodiments of the flossing head 300 are presented in FIGS. 11A, 11B, 12A, 12B and 12C. These embodiments are designated as generally as angled flossing head 400 and straight flossing head 500. As these embodiments are very similar to embodiment 300, the last two digits of similar parts will be identical to those of embodiment 300. The only significant difference between embodiment 300 and embodiment 400 of the flossing head is that link 310 has been replaced by flexible member 450 which is closely guided by curved bore 451 in angled tip 402. Flexible member 450 may be made from a tough flexible plastic such as nylon or from a small diameter flexible stainless steel wire rope. FIGS. 11A and 11B show the connection of floss assembly 600. Floss assemblies 600A, 600B and 600C may also be used with the suitable modifications to flexible member 450 similar to those shown in FIGS. 10A, 10B, 10C and 10D. It should also be noted that a similar flexible member could be used in place of link 710 in the non-powered unit 700.

Figure 12A:
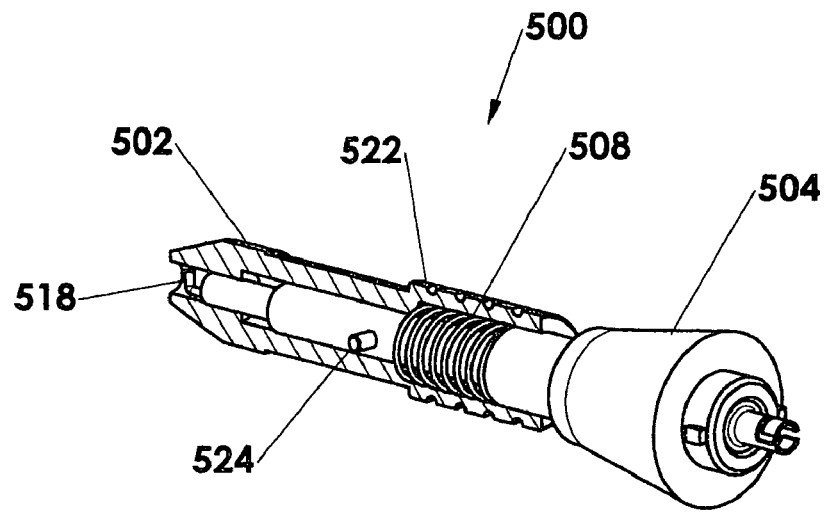
FIG. 12A is a cross-sectional perspective view of the second embodiment of the flossing head in the latched position.
Figure 12B:
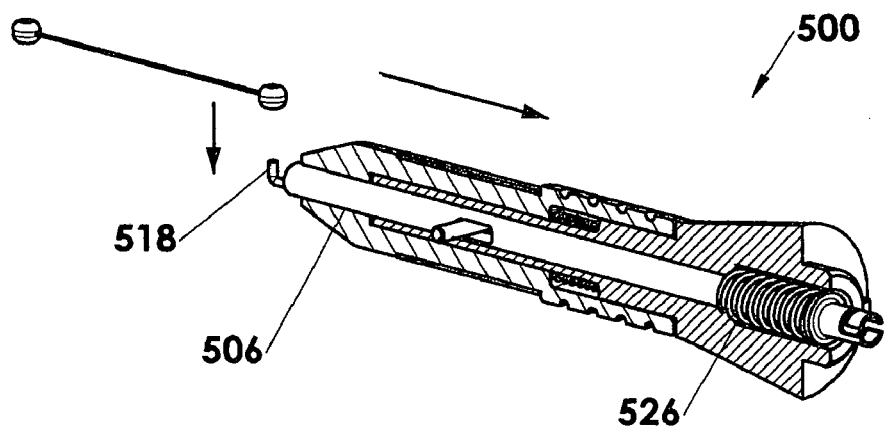
FIG. 12B is a cross-sectional perspective view of the second embodiment of the flossing head in the unlatched position.
Figure 12C:
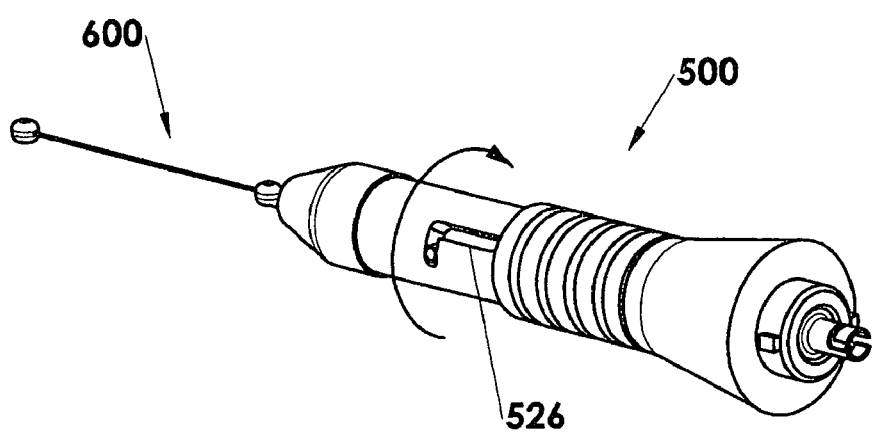
FIG. 12C is a cross-sectional perspective view of the second embodiment of the flossing head in the unlatched and locked position with the first embodiment of the floss assembly attached.
Figure 13A:
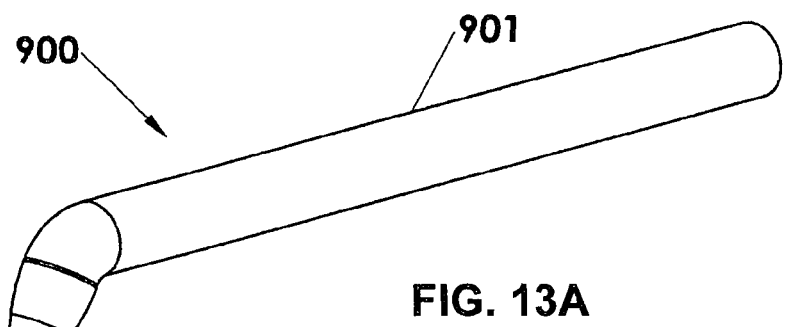
FIG. 13A is a perspective of a first embodiment of a disposable angled non-powered floss handle.
Figure 13B:
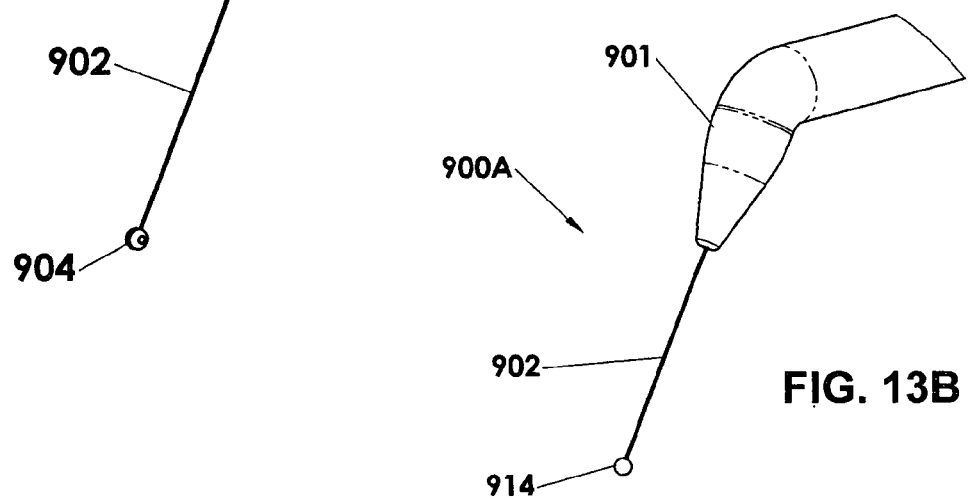
FIG. 13B is a fragmentary perspective of a second embodiment of a disposable angled non-powered floss handle.
Figure 13C:
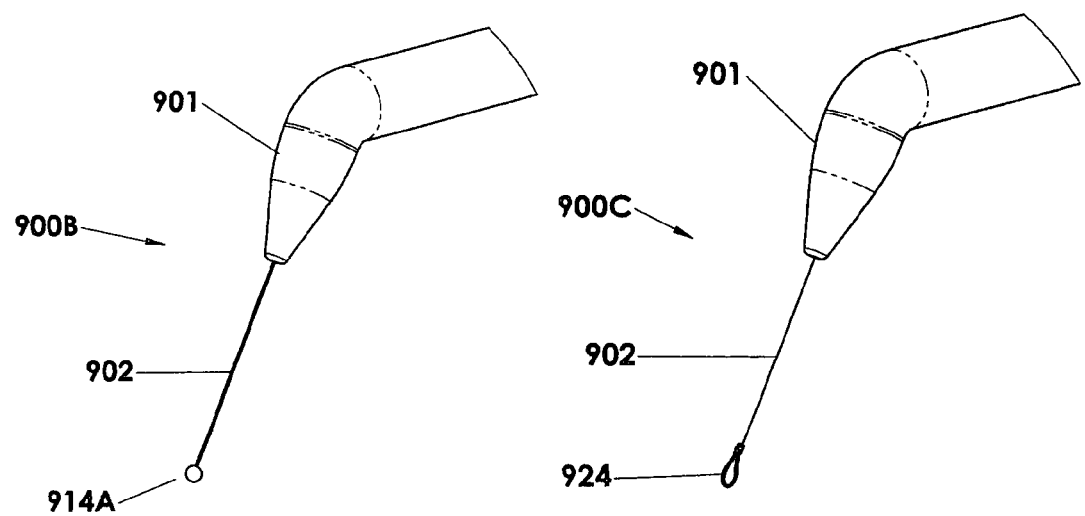
FIG. 13C is a fragmentary perspective of a third embodiment of a disposable angled non-powered floss handle.
Figure 13D:
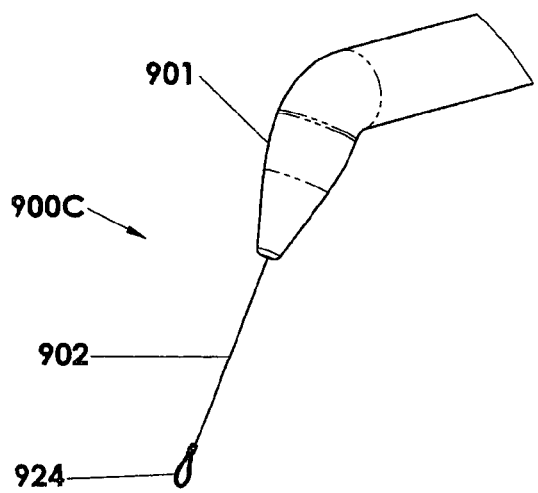
FIG. 13D is a fragmentary perspective of a fourth embodiment of a disposable angled non-powered floss handle.

As shown in FIGS. 12A, 12B and 12C, embodiment 500 of the flossing head eliminates the angled tip of embodiment 300 and replaces it with the straight tip 502. This simplification eliminates the need for the link 310 and pins 312 and 314, and allows the L-shaped hook 518 to be fixably attached directly to the drive shaft 506. Attachment of floss assembly 600 remains the same. As with the angled flossing head 400, floss assemblies 600A, 600B or 600C could also be used with the suitable modifications to floss connection L-shaped hook 518 or by adding a slotted socket to the end of shaft 506 similar to those shown in FIGS. 10A, 10B, 10C and 10D. FIG. 12C shows the use of L-shaped slot 526 to lock the straight flossing tip 502 in the unlatched position. This is accomplished by the user manually rotating the tip 502 approximately 30 degrees about the longitudinal axis as indicated by the arrow. This feature is used to simplify floss attachment and can be adapted to any of the embodiments of the straight flossing head or embodiments of the straight non-powered units. It can also be adapted to the angled flossing head 400 with the flexible drive member 450.

Figure 8A:
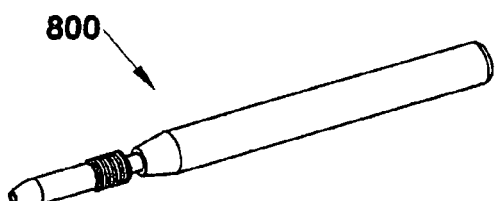
FIG. 8A is a perspective view of the second embodiment of the non-powered floss handle.
Figure 8B:
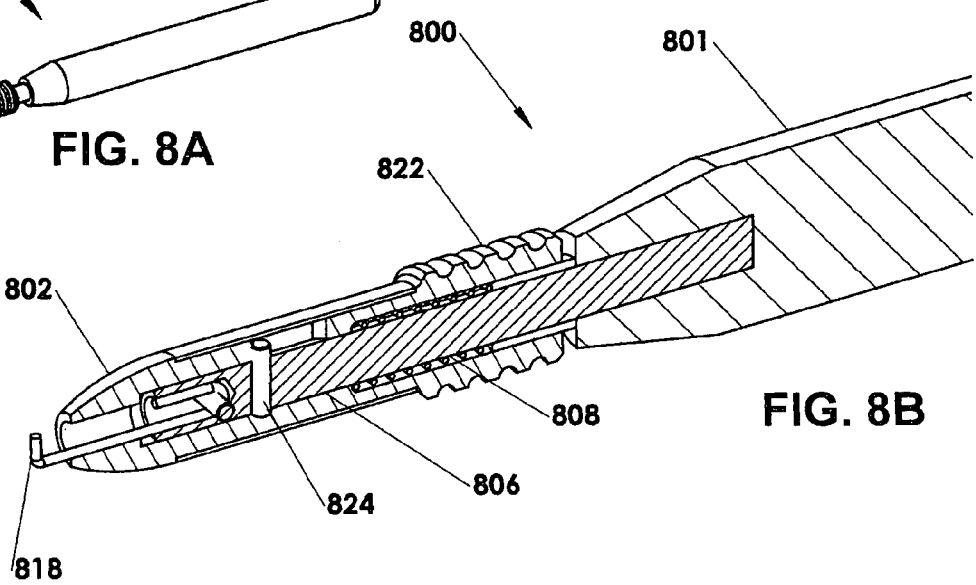
FIG. 8B is a fragmentary partial cross-sectional perspective view of the second embodiment of the non-powered floss handle designed for use with the first embodiment of the floss assembly.

A further embodiment of the non-powered flossing unit 700 is designated as unit 800 and shown in FIGS. 8A and 8B. This embodiment mimics the difference between embodiments 400 and 500 of the flossing head in that it incorporates a straight tip 802 instead of the angled tip 702 and has a modified attachment of hook 818 to the shaft 806.

Disposable embodiments of the non-powered flossing unit designated as 900, 900A, 900B and 900C have angled tips (FIGS. 13A-13D) while units designated 1000, 1000A, 1000B, and 1000C have straight tips (FIGS. 14A-14D). The embodiments 900 and 1000 have a plastic bead 904 or 1004 attached at the free end of the floss 902 or 1002 respectively. The embodiments 900A and 1000A have a plastic ball 914 or 1014 attached at the free end of the floss 902 or 1002 respectively. The embodiments 900B and 1000B have a metal ball 914A or 1014A attached at the free end of the floss 902 or 1002 respectively; and finally, the embodiments 900C and 1000C have a loop 924 or 1024 tied into the free end of the floss 902 or 1002 respectively. These embodiments fix (e.g., permanently) one end of the disposable floss assembly to the disposable handle, thus eliminating all internal mechanism in the non-powered unit and so as to reduce the complexity and cost of the units. That is, there is no detachable coupling between the floss assembly and the handle in this case. As used herein, the term "attached" covers both a detachable and fixed interconnection between the two noted components. Each of these various types of disposable floss and handle assemblies would by used in conjunction with the appropriate embodiment of the powered flossing head.

What is claimed is:

1. A flossing device, comprising:
   a first handle comprising a first aperture, a drive, and a drive shaft that is interconnected with said drive and that axially reciprocates relative to said first aperture during operation of said drive, wherein said first aperture has a closed perimeter;
   a second handle, wherein said first and second handles are independently maneuverable by a user's first and second hands, respectively; and
   dental floss, wherein said dental floss is interconnected with said second handle, wherein said dental floss extends through said first aperture to interconnect with said drive shaft of said first handle such that an entirety of said dental floss reciprocates along a length dimension of said dental floss and relative to said first aperture when said dental floss is tensioned, and wherein a segment of said dental floss that is located between said first and second handles may be disposed between a pair of adjacent teeth:
   wherein said first handle comprises a first fitting, wherein said dental floss comprises a first dental floss fitting, wherein said first fitting and said first dental floss fitting are detachably coupled, wherein said second handle comprises a second fitting, wherein said dental floss comprises a second dental floss fitting, wherein said second fitting and said second dental floss fitting are detachably coupled, and wherein said first fitting is interconnected with said drive shaft such that said first fitting axially reciprocates during operation of said drive; and
   wherein said first handle comprises a first distal end as well as first and second sections, wherein said first section is movably interconnected with said second section and comprises said first distal end, wherein relative movement between said first and second sections causes said first fitting to move relative to said first section and extend beyond said first distal end of said first section, wherein said second handle comprises a second distal end as well as third and fourth sections, wherein said third section is movably interconnected with said fourth section and comprises said second distal end, wherein said second fitting is interconnected with said fourth section, wherein relative movement between said third and fourth sections causes said second fitting to move relative to said third section and extend beyond said second distal end of said third section.

2. The flossing device of claim 1, wherein said second handle is non-powered.

3. The flossing device of claim 1, wherein said second handle comprises a second aperture having a closed perimeter, wherein said dental floss extends through said second aperture to interconnect with said second handle.

4. The flossing device of claim 3, wherein said first and second handles comprise first and second internal bores, respectively, wherein an intersection of said first internal bore with said first distal end defines said first aperture, and wherein an intersection of said second internal bore with said second distal end defines said second aperture.

5. The flossing device of claim 1, wherein an interconnection between said dental floss and said drive shaft remains within an interior of said first handle during operation of said flossing device, and wherein an interconnection between said dental floss and said second handle remains within an interior of said second handle during operation of said flossing device.

6. The flossing device of claim 1, wherein said first fitting and said first dental floss fitting remain recessed within said first handle during operation of said flossing device, and wherein said second fitting and said second dental floss fitting remain recessed within said second handle during operation of said flossing device.

7. The flossing device of claim 1, wherein said first fitting is disposable in first and second positions, wherein said first fitting is exposed in its said first position and is recessed within said first handle in its said second position, wherein said second fitting is disposable in first and second positions, wherein said second fitting is exposed in its said first position and is recessed within said second handle in its said second position.

8. The flossing device of claim 1, wherein said drive shaft and said first fitting are interconnected by a first linkage.

9. The flossing device of claim 1, wherein a first detachably coupled condition exists when said first fitting and said first dental floss fitting are detachably coupled, wherein said first detachably coupled condition comprises a magnetic interaction between said first fitting and said first dental floss fitting, wherein a second detachably coupled condition exists when said second fitting and said second dental floss fitting are detachably coupled, wherein said second detachably coupled condition comprises a magnetic interaction between said second fitting and said second dental floss fitting.

10. The flossing device of claim 1, wherein said first handle comprises a magnet that magnetically interacts with said first dental floss fitting.

11. The flossing device of claim 10, wherein said first fitting comprises a socket that in turn comprises a slot, wherein said first dental floss fitting is received in said socket, and wherein said dental floss extends through said slot.

12. A flossing device, comprising:
    a first handle comprising a first section and a first fitting, wherein said first section comprises a first distal end and a first internal bore that extends to said first distal end, wherein said first fitting is disposable within said first internal bore, wherein said first fitting is movable relative to said first section such that said first fitting moves relative to and along said first internal bore so as to be disposed beyond said first distal end in a coupling/decoupling position where said first fitting is exposed, and wherein said first fitting is movable relative to said first section such that said first fitting moves relative to, into, and along said first internal bore such that said first fitting is disposable in an operating position where said first fitting remains recessed within said first handle, wherein said first handle further comprises a drive and a drive shaft that is interconnected with and moved by operation of said drive, wherein said first fitting is interconnected with said drive shaft such that said first fitting is also moved by operation of said drive;
    a second handle, wherein said first and second handles are independently maneuverable by a user's first and second hands, respectively; and
    dental floss comprising a first dental floss fitting in a first detachably coupled condition with said first fitting, wherein said first detachably coupled condition is established when said first fitting is in its said coupling/decoupling position, wherein said first dental floss fitting remains recessed within said first handle when said first fitting is in its said operating position and with said first dental floss fitting and said first fitting being in said first detachably coupled condition, wherein said dental floss is attached to said second handle, and wherein a segment of said dental floss that is located between said first and second handles may be disposed between a pair of adjacent teeth.

13. The flossing device of claim 12, wherein said drive shaft axially reciprocates during operation of said drive, wherein said first fitting is interconnected with said drive shaft such that said first fitting also axially reciprocates during operation of said drive, and wherein said second handle is non-powered.

14. The flossing device of claim 12, wherein said second handle comprises a second section and a second fitting, wherein said second section comprises a second distal end and a second internal bore that extends to said second distal end, wherein said second fitting is disposable within said second internal bore, wherein said dental floss comprises a second dental floss fitting in a second detachably coupled condition with said second fitting, wherein said second fitting is movable relative to said second section such that said second fitting moves relative to and along said second internal bore so as to be disposed beyond said second distal end in a coupling/decoupling position where said second fitting is exposed, wherein said second fitting is movable relative to said second section such that said second fitting moves relative to, into, and along said second internal bore such that said second fitting is disposable in an operating position where said second fitting remains recessed within said second handle, wherein said second detachably coupled condition is established when said second fitting is in its said coupling/decoupling position, and wherein said second dental floss fitting remains recessed within said second handle when said second fitting is in its said operating position and with said second dental floss fitting and said second fitting being in said second detachably coupled condition.

15. The flossing device of claim 14, wherein said first handle further comprises a third section, wherein said first section is movably interconnected with said third section, wherein relative movement between said first and third sections causes said first fitting to move relative to said first section and extend beyond said first distal end of said first section and which corresponds with said coupling/decoupling position of said first fitting, wherein said second handle further comprises a fourth section, wherein said second section is movably interconnected with said fourth section, wherein relative movement between said second and fourth sections causes said second fitting to move relative to said second section and extend beyond said second distal end of said second section and which corresponds with said coupling/decoupling position of said second fitting.

16. The flossing device of claim 14, wherein said first detachably coupled condition comprises a magnetic interaction between said first fitting and said first dental floss fitting, and wherein said second detachably coupled condition comprises a magnetic interaction between said second fitting and said second dental floss fitting.

17. The flossing device of claim 12, wherein said drive shaft and said first fitting are interconnected by a first linkage.

18. The flossing device of claim 12, wherein said first detachably coupled condition comprises a magnetic interaction between said first fitting and said first dental floss fitting.

19. The flossing device of claim 12, wherein said first handle comprises a magnet that magnetically interacts with said first dental floss fitting.

20. The flossing device of claim 19, wherein said first fitting comprises a socket that in turn comprises a slot, wherein said first dental floss fitting is received in said socket, and wherein said dental floss extends through said slot.

* * * * *